US008854734B2

(12) United States Patent
Ingram

(10) Patent No.: US 8,854,734 B2
(45) Date of Patent: Oct. 7, 2014

(54) INTEGRATING OPTICAL SYSTEM AND METHODS

(75) Inventor: Michael W. Ingram, Austin, TX (US)

(73) Assignee: Vela Technologies, Inc., San Diego, CA (US)

(*) Notice: Subject to any disclaimer, the term of this patent is extended or adjusted under 35 U.S.C. 154(b) by 505 days.

(21) Appl. No.: 12/639,407

(22) Filed: Dec. 16, 2009

(65) Prior Publication Data

US 2011/0108741 A1    May 12, 2011

Related U.S. Application Data

(60) Provisional application No. 61/260,766, filed on Nov. 12, 2009.

(51) Int. Cl.
*G02B 5/02*     (2006.01)
*G02B 13/20*    (2006.01)
*G01N 21/47*    (2006.01)
*G02B 19/00*    (2006.01)

(52) U.S. Cl.
CPC ............ *G02B 5/0278* (2013.01); *G01N 21/474* (2013.01); *G01N 21/4738* (2013.01); *G01N 2021/4754* (2013.01); *G01N 2201/0634* (2013.01); *G01N 2201/065* (2013.01); *G02B 5/0284* (2013.01); *G02B 19/0085* (2013.01); *G02B 19/0071* (2013.01); *G02B 19/009* (2013.01); *G02B 19/0028* (2013.01)
USPC ........... 359/599; 359/707; 356/236; 356/445; 356/446

(58) Field of Classification Search
CPC ...... G02B 5/02; G02B 5/0273; G01N 21/474; G01N 21/553; G01N 29/265; G01J 2001/0481; G01M 3/005
USPC .......................... 359/599, 387, 613–614, 707
See application file for complete search history.

(56) References Cited

U.S. PATENT DOCUMENTS

| 3,872,349 | A |   | 3/1975  | Spero et al. |
| 3,911,318 | A |   | 10/1975 | Spero et al. |
| 4,042,850 | A |   | 8/1977  | Ury et al. |
| 4,062,996 | A |   | 12/1977 | Keafer, Jr. et al. |
| 4,232,971 | A | * | 11/1980 | Suga .............................. 356/446 |
| 4,313,969 | A |   | 2/1982  | Matthews et al. |
| 4,583,860 | A |   | 4/1986  | Butner |
| 4,659,193 | A | * | 4/1987  | Nagano ......................... 359/387 |

(Continued)

OTHER PUBLICATIONS

Chin et al., "Integrating Sphere Sources for UV Exposure: A Novel Approach to the Artificial UV Weathering of Coatings, Plastics, and Composites", 2002, pp. 144-160, Methodology and Metrologies, American Chemical Society Symposium Series 805.

(Continued)

*Primary Examiner* — Thong Nguyen
(74) *Attorney, Agent, or Firm* — Fitch, Even, Tabin & Flannery, LLP

(57) ABSTRACT

An integrating optical system having a chamber, the chamber having an aperture and at least one portion having a diffuse reflective material; a light source; and a diffuse transmissive baffle. The baffle is located in relation to the chamber such that it is also located in an optical path between the light source and a treatable target. A light-ray originating from the light source is diffusely transmitted from the diffuse transmissive baffle and impinges on an interior surface of the chamber before impinging on the treatable target.

36 Claims, 24 Drawing Sheets

(56) References Cited

U.S. PATENT DOCUMENTS

| | | | |
|---|---|---|---|
| 4,839,522 A | | 6/1989 | Bourgeois et al. |
| 4,880,677 A | | 11/1989 | Hecq et al. |
| 4,907,887 A | | 3/1990 | Leonard |
| 5,251,004 A | | 10/1993 | Doiron et al. |
| 5,268,749 A | * | 12/1993 | Weber et al. ............... 356/446 |
| 5,497,004 A | | 3/1996 | Rudolph et al. |
| 5,517,315 A | | 5/1996 | Snail et al. |
| 5,689,364 A | | 11/1997 | McGregor et al. |
| 5,745,234 A | | 4/1998 | Snail et al. |
| 5,777,244 A | * | 7/1998 | Kumagai et al. ............. 73/865.8 |
| 5,781,342 A | | 7/1998 | Hannon et al. |
| 5,820,250 A | * | 10/1998 | Betts et al. .................. 362/216 |
| 5,903,091 A | | 5/1999 | MacLennan et al. |
| 6,005,249 A | | 12/1999 | Hayes, Jr. et al. |
| 6,007,225 A | * | 12/1999 | Ramer et al. ................. 362/554 |
| 6,166,389 A | | 12/2000 | Shie et al. |
| 6,222,623 B1 | | 4/2001 | Wetherell |
| 6,226,085 B1 | | 5/2001 | Weber |
| 6,229,328 B1 | | 5/2001 | Lueders |
| 6,424,413 B1 | | 7/2002 | Weber |
| 6,583,879 B1 | | 6/2003 | Berg et al. |
| 6,626,052 B1 | | 9/2003 | Martin et al. |
| 6,636,363 B2 | * | 10/2003 | Kaminsky et al. ............ 359/707 |
| 6,737,637 B1 | * | 5/2004 | Balster et al. ................ 250/228 |
| 6,866,899 B2 | | 3/2005 | Wright |
| 7,057,821 B2 | * | 6/2006 | Zincone ........................ 359/595 |
| 7,121,690 B1 | * | 10/2006 | Ramer et al. ................. 362/297 |
| 7,248,350 B2 | | 7/2007 | Kettler |
| 7,401,943 B2 | | 7/2008 | Okamitsu et al. |
| 7,508,503 B2 | | 3/2009 | Jang |
| 7,532,324 B2 | | 5/2009 | Liu |
| 2005/0023478 A1 | | 2/2005 | Ruckman et al. |
| 2005/0115498 A1 | | 6/2005 | Ingram et al. |
| 2008/0013082 A1 | | 1/2008 | Cutlip |
| 2008/0129996 A1 | | 6/2008 | Liu |
| 2008/0204705 A1 | * | 8/2008 | Liu .................................. 356/30 |
| 2008/0262117 A1 | | 10/2008 | Avakian et al. |
| 2008/0285276 A1 | | 11/2008 | Okamitsu et al. |

OTHER PUBLICATIONS

Hoffman Sphereoptics, "Integrating Sphere Design and Applications, Technical Information," 2004, pp. 1-20, Hoffman SphereOptics, Concord, NH.

Pike Technologies, "Integrating Spheres—Introduction and Theory," 2005, pp. 1-2, Pike Technologies, Madison, WI.

Saunders et al., "Roughened Quartz Surfaces and Teflon as small angle diffusers and depolarizers between 200 and 400 nm," Aug. 1, 1989, pp. 3242-3245, Applied Optics, vol. 28, No. 15, Gaithersburg, MD.

The Dow Chemical Company, Chin et al., "Ultraviolet Chambers based on Integrating Spheres for Use in Artificial Weathering," Nov. 5, 2001, pp. 1-17, The Proceedings of the 70$^{th}$ Annual Meeting, Technical Program of the FSCT, Atlanta, Georgia.

Gigahertz-Optik, "Diffuse Reflectors", Nov. 16, 2004, pp. 123-130, Gigahertz-Optik, Germany.

Labsphere, "A Guide to Integrating Sphere Radiometry and Photometry, Tech Guide," May 30, 2008, pp. 1-25, Labsphere Inc., North Sutton, NH.

Labsphere, "A Guide to Integrating Sphere Theory and Applications, Tech Guide," Apr. 24, 2008, pp. 1-19, Labsphere Inc., North Sutton, NH.

Labsphere, "Optical-Grade Spectralon Material," Apr. 30, 2008, pp. 1-2, Labsphere Inc., North Sutton, NH.

Optronic Laboratories, "Optolon 2: The Integrating Sphere Coating of the Future," Oct. 13, 2008, pp. 1-3, Optronic Laboratories, Orlando, FL.

Cambridge Dictionary, "Diffuse Reflection," May 1, 2012, pp. 1, published at http://web.archive.org/web/20120501061758/http://dictionary.cambridge.org/dictionary/american-english/diffuse-reflection.

Dr. Jeffrey L. Talor, "Tales From the Solar Industry (Part 1): How to Measure Specular Reflectance Samples on a 60 mm Integrating Sphere and Obtain Accurate Results," Perkin Elmer Article, Nov. 16, 2009, pp. 1-9, published at http://pe.taylorjl.net/PE_Blog/?p=260.

Exfo, "Catheter Assembly," Sep. 7, 2010, p. 1, published at http://www.exfo-omnicure.com/applications-catheter-assembly.php?tab=1.

Exfo, "Cure Ring," Sep. 8, 2010, pp. 1-3, published at http://www.exfo-omnicure.com/products-cure-ring-a.php.

Exfo, "OmniCure Assembly Solutions: Ablation Catheters," Oct. 16, 2009, pp. 1-5, published on Oct. 16, 2009, Exfo, Mississauga, Ontario, Canada.

Exfo, "OmniCure Assembly Solutions: Bonding of Balloon Catheters," Aug. 4, 2009, pp. 1-5, published on Aug. 4, 2009, Exfo, Mississauga, Ontario, Canada.

Exfo, "OmniCure Cure Ring Radiometer," Sep. 8, 2010, pp. 1-2, published at http://www.exfo-omnicure.com/products-cure-ring.php.

JH Technologies, "Exfo Cure Ring," Sep. 8, 2010, pp. 1-2, published at http://www.jhtechnologies.com/uvcuring/opecr.shtml.

Martin Janecek and William W. Moses, "Optical Reflectance Measurements for Commonly Used Reflectors," Journal of Nuclear Science, Aug. 2008, pp. 2432-2437, vol. 55, Issue 4.

Michael Oren and Shree K. Nayar, "Generalization of Lambert's Reflectance Model," 1994, pp. 239-246, published in the Proceedings of the 21$^{st}$ conference on Computer graphics and interactive techniques.

Photokonnexion, "Diffuse Reflection," May 3, 2013, pp. 2, published at http://www.photokonnexion.com/?page_id=10043.

SIGGRAPH, "Diffuse Relection," Feb. 14, 2009, pp. 2, published at http://web.archive.org/web/20090214002550/http://siggraph.org/education/materials/hypergraph/illumin/diffuse_reflection.htm.

Wikipedia, "Diffuse Reflection," Mar. 24, 2005, pp. 1, published at http://web.archive.org/web/20050324015620/http://en.wikipedia.org/wiki/Diffuse_reflection.

Wikipedia, "Visual Appearance," May 7, 2005, pp. 1-5, published at http://web.archive.org/web/20090507051309/http://en.wikipedia.org/wiki/visual_appearance.

\* cited by examiner

INTEGRATING OPTICAL SYSTEM AND METHODS

This application claims the benefit of U.S. Provisional Application No. 61/260,766, filed Nov. 12, 2009, which is incorporated in its entirety herein by reference.

BACKGROUND OF THE INVENTION

1. Field of the Invention

The present invention technically relates to optical systems and methods. More particularly, the present invention technically relates to integrating optical systems and methods.

2. Disclosure of the Related Art

In the related art, conventional integrating sphere systems are typically used for characterizing the surface properties of materials. Integrating spheres, also termed Ulbricht spheres, are optical apparati typically comprising a hollow spherical cavity with its interior having a high diffuse reflectivity for providing a largely uniform scattering or diffusing effect. The spheres typically have relatively small ports functioning as entrance and exit ports. Light-rays incident on any point on the inner surface are, by multiple scattering reflections, uniformly distributed to all other such points, thereby minimizing the effect of the light's original direction. An integrating sphere preserves power, but destroys spatial information. It is typically used with a light source and a detector for making optical power measurements. Also, related art integrating sphere systems may comprise only diffuse reflecting elements, e.g., diffuse reflecting baffles, which effect a high total reflectance and essentially no transmission, but endeavor to improve the uniformity of the irradiance at an output port. Such related art diffuse reflecting baffles tend to be small in size, because either the ports are small or the light being input has a low divergence, e.g., from a laser beam. As such, the related art diffuse reflecting baffles have little effect on the overall irradiance within an integrating sphere. Examples of typical related art integrating spheres are explained as follows.

Referring to FIG. 1A, this interior view schematic diagram, illustrates a conventional integrating sphere system 100, comprising a housing 5 having an input port 60, and an output port 70, a light source 10 disposed outside the housing 5, a detector 20 disposed outside the housing 5, a diffuse reflective baffle 30 disposed at a far surface of the housing 5, wherein a first incidence of light 40 originating from the light source 10 is diffusely reflected from the far surface of the housing 5, wherein some of the diffusely reflected light is incident on reflective baffle 30, wherein the detector has an approximate field-of-view 50, and wherein the field-of-view 50 does not contain any rays directly incident from the source 10, in accordance with the related art.

Referring to FIG. 1B, this interior view schematic diagram illustrates a conventional integrating sphere system 101, comprising a housing 5 having an output port 70, a light source 10 disposed inside the housing 5, a detector 20 disposed outside the housing 5, a diffuse reflective baffle 30 disposed between light source 10, and detector 20 disposed outside the housing 5, wherein light originating from the light source 10 is diffusely reflected from an interior surface of the housing 5, wherein some of the diffusely reflected light is incident on reflective baffle 30, wherein the detector has an approximate field-of-view 50, and wherein the field-of-view 50 does not contain any rays directly incident from the source 10, in accordance with the related art.

Referring to FIG. 1C, this interior view schematic diagram illustrates a conventional integrating sphere system 102, comprising a housing 5 having an output port 70, a light source 10 disposed inside the housing 5, a detector 20 disposed outside the housing 5, a diffuse reflective baffle 30 disposed at a near surface between the light source 10 and the output port 70, and detector 20 disposed outside the housing 5, wherein light originating from the light source 10 is diffusely reflected from an interior surface of the housing 5, wherein some of the diffusely reflected light leaves the output port 70 as output radiation 71, wherein some of the diffusely reflected light is incident on the diffuse reflective baffle 30, and wherein none of the light from the source 10 is directly incident on the detector 20, in accordance with the related art.

The foregoing conventional integrating spheres are typically used for making a variety of optical, photometric, and radiometric measurements, such as quantifying the total of the light radiated in all directions from a lamp, measuring diffuse reflectance of surfaces, while properly averaging over all angles of illumination and observation, creating a light source with apparent intensity generally uniform over all positions within its circular aperture, and independent of direction except for the cosine function inherent to ideally diffuse radiating surfaces, accurately measuring the sum of all the ambient light incident on a small circular aperture, and measuring the power in the laser beam, with best available independence of beam details such as beam shape, incident direction, and incident position.

In addition to conventional integrating spheres, diffuse reflective surfaces and diffuse transmissive surfaces have been known in the related art for altering the pathway of light. FIGS. 2A and 2B show the manner in which light behaves when impinging such surfaces. FIG. 2A illustrates, in a schematic diagram, a pathway of an incident light-ray 90 on a diffuse reflective surface 80, wherein the incident light-ray 90 is diffusely reflected at various angles as reflected light-rays 95, in accordance with the related art. That is, the diffuse reflective surface 80 scatters the incident light ray substantially uniformly into all directions in a hemisphere adjacent to an incident side of the diffuse reflective surface, including an incoming direction of the incident light ray. Therefore, in some cases, the diffuse reflective surface 80 is an isotropic material and produces a reflectance that is substantially Lambertian. FIG. 2B illustrates, in a schematic diagram, a pathway of an incident light-ray 90 on a diffuse transmissive surface 85, wherein the incident light-ray 90 is diffusely transmitted at various angles as transmitted light-rays 97, in accordance with the related art. That is, the diffuse transmissive surface 85 transmits and scatters the incident light-ray substantially uniformly into all directions in a hemisphere adjacent to a through side of the diffuse transmissive surface 85. Transmitting diffusers have been used on detectors in the related art only as cosine-collectors for eliminating the detector's sensitivity to an incident angle of incoming light.

SUMMARY OF THE INVENTION

Several embodiments of the invention advantageously address the needs above as well as other needs by providing a diffusely transmissive optical integrating system and its related methods.

In one embodiment, the invention can be characterized as an integrating optical system, comprising: at least one chamber, each at least one chamber having at least one aperture and at least one portion comprising a diffuse reflective material; at least one light source; and at least one diffuse transmissive baffle disposed in relation to the at least one chamber in a manner wherein the at least one diffuse transmissive baffle is also disposed in an optical path between the at least one light source and at least one treatable target, wherein at least one light-ray originating from the at least one light source is diffusely transmitted from the at least one diffuse transmissive baffle and impinges on an interior surface of the at least one chamber before impinging on the at least one treatable target.

In another embodiment, the invention can be characterized as a method of fabricating an integrating optical system, providing at least one chamber having at least one aperture and at least one portion comprising a diffuse reflective material; providing at least one light source; and providing at least one diffuse transmissive baffle disposed in relation to the at least one chamber in a manner wherein the at least one diffuse transmissive baffle is also disposed in an optical path between the at least one light source and at least one treatable target, wherein the at least one diffuse transmissive baffle is disposed in a manner wherein at least one light-ray originating from the at least one light source is diffusely transmittable from the at least one diffuse transmissive baffle and impingeable on an interior surface of the at least one chamber before being impingeable on the at least one treatable target.

In a further embodiment, the invention may be characterized as a method of treating at least one treatable target with light, comprising: providing light, having at least one light-ray, within a volume from at least one light source; diffusely transmitting the at least one light-ray being in a direct path to the at least one treatable target by way of at least one diffuse transmissive baffle such that the at least one light-ray impinges on an interior surface of at least one chamber before impinging on the at least one treatable target; diffusely reflecting the at least one light-ray within the volume for collecting the at least one light, thereby integrating the at least one light-ray, and thereby providing at least one integrated light-ray; and irradiating the at least one treatable target with the at least one integrated light-ray, thereby providing at least one treated target.

BRIEF DESCRIPTION OF THE DRAWINGS

The foregoing aspects, features, and advantages, inter alia, of the several embodiments in the present invention will be more apparent from the following more particular description thereof, presented in conjunction with the following drawings.

Figure 1A:
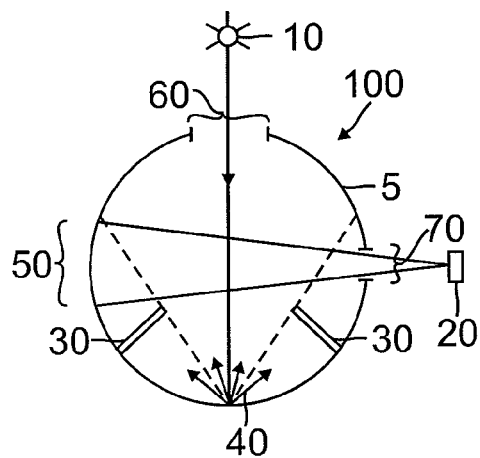
FIG. 1A is a schematic diagram of a conventional integrating sphere system, comprising a housing, a light source disposed outside the housing, a detector disposed outside the housing, and a reflective baffle disposed at a far surface of the housing, in accordance with the related art.
Figure 1B:
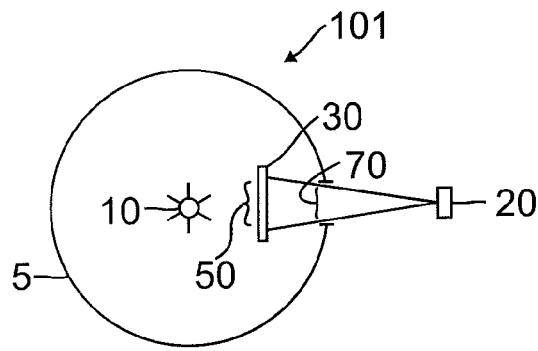
FIG. 1B is a schematic diagram of a conventional integrating sphere system, comprising a housing, a light source disposed inside the housing, a detector disposed outside the housing, a reflective baffle disposed in the housing between the light source and a detector, the detector disposed outside the housing, in accordance with the related art.
Figure 1C:
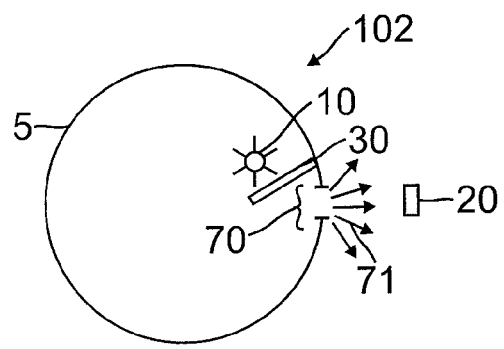
FIG. 1C is a schematic diagram of a conventional integrating sphere system, comprising a housing, a light source disposed inside the housing, a detector disposed outside the housing, a reflective baffle disposed inside the housing at a near surface between the light source and an output port, and a detector disposed outside the housing, in accordance with the related art.
Figure 2A:
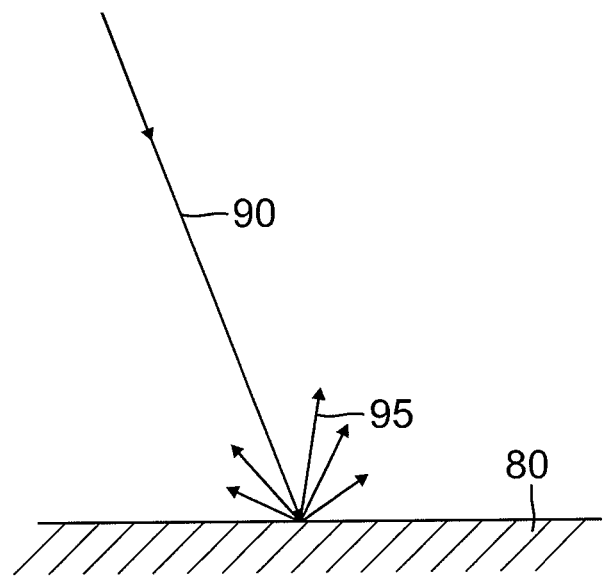
FIG. 2A is a schematic diagram showing a pathway of an incident light-ray on a diffuse reflective surface, wherein the light is diffusely reflected at various angles as reflected light-rays, in accordance with the related art.
Figure 2B:
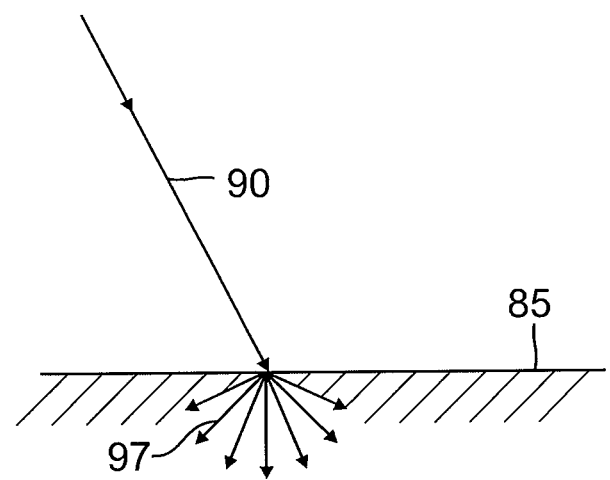
FIG. 2B is a schematic diagram showing a pathway of an incident light-ray on a diffuse transmissive surface, wherein the light is diffusely transmitted at various angles as transmitted light-rays, in accordance with the related art.

Corresponding reference characters and numerals indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to facilitate improving the understanding of various embodiments of the present invention. Also, conventional, but well-understood, elements, that are useful or necessary in a commercially feasible embodiment, are often not depicted in order to provide a less-obstructed view of these various embodiments of the present invention.

DETAILED DESCRIPTION OF THE INVENTION

The following detailed description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic, described in connection with the embodiment, is included in at least one embodiment of the present invention. Thus, appearances of the phrases "in one embodiment," "in an embodiment," and similar language throughout this specification may, but do not necessarily, all refer to the same embodiment.

Although diffuse reflective surfaces, diffuse transmissive surfaces, and integrating spheres have been individually known in the related art, their combination, especially for treating work-pieces, is not believed to be hitherto known. In some embodiments of the invention, an integrating optical system is provided that comprises at least one chamber, each at least one chamber having at least one aperture and at least one portion comprising a diffuse reflective material; at least one light source; and at least one diffuse transmissive baffle disposed in relation to the at least one chamber in a manner wherein the at least one diffuse transmissive baffle is also disposed in an optical path between the at least one light source and at least one treatable target, wherein at least one light-ray originating from the at least one light source is diffusely transmitted from the at least one diffuse transmissive baffle and impinges on an interior surface of the at least one chamber before impinging on the at least one treatable target. In some cases, a related art integrating sphere, having a chamber and using only a diffuse reflecting baffle, is not conducive for use in curing objects using ultraviolet light, because a very large chamber would be required to accommodate an effective diffuse reflecting baffle, additional total reflecting area would be required, thereby reducing irradiance, the allowable input power would be limited, thereby reducing the irradiance within the chamber, and fabrication cost of the chamber would increase. Further, some embodiments of the present invention involve an integrating optical system that performs functions beyond mere measurement and characterization, that both internally and externally accommodates a work-piece, that can optically treat the work-piece, that decreases the infrared (IR) component of lamp radiation incident on the work-piece, that substantially absorbs the IR component, that controls the ratio between the IR component and the ultraviolet (UV) component, and that provides a substantially uniform irradiance for treating a target.

Several embodiments of the present invention advantageously address the needs in the related art, as well as other needs, in a diffusely transmissive optical integrating system, that performs functions beyond mere measurement and characterization, that both internally and externally accommodates a work-piece, and that can optically treat the work-piece, and its associated methods. In addition, some embodiments of the present invention address back-reflection of light in the visible and IR wavelengths, thereby preventing them from being incident on the work-piece and from degrading the UV curing process. Also, some embodiments of the present invention address the issue of absorption of IR light by diffuse reflectors that tends to cause thermal damage to the diffuse reflector in high irradiance applications. In particular, some embodiments of the present invention system and methods involve a diffuse transmissive element, e.g., a diffuse transmissive baffle, which substantially reduces the IR power density incident on diffuse reflective surfaces in the chamber, thereby reducing damage to those diffuse reflective surfaces. A uniform irradiance is desired in some embodiments of the present invention, especially for treating a target.

Figure 3A:
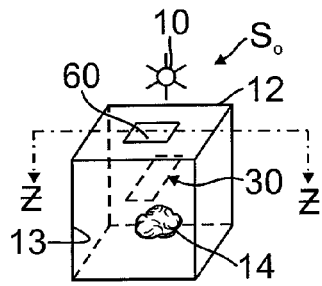
FIG. 3A is an interior perspective view schematic diagram of an integrating optical system, comprising an integrating chamber, a light source, a diffuse reflective baffle disposed within the chamber and between the light source and a work-piece, the work-piece disposed within the chamber, in accordance with an embodiment.

Referring to FIG. 3A, this interior perspective view schematic diagram illustrates an integrating optical system $S_O$, having a center plane Z-Z and comprising an integrating chamber or a chamber 12, the chamber 12 having an input port 60 and a diffusely reflecting interior surface 13, a light source 10 disposed outside the chamber 12, a diffuse reflective baffle 30 disposed within the chamber 12 and between the light source 10 and a work-piece, such as a treatable target 14, disposed inside the chamber 12, wherein light is diffusely reflected from the interior surface of the chamber 12, wherein light is diffusely reflected by the diffuse reflective baffle 30 and then onto either the interior surface of the chamber 12 or out of the chamber 12 through the input port 60, wherein some of the diffusely reflected light is incident upon the treatable target 14, whereby the treatable target 14 is treated by the diffusely reflected light in accordance with an embodiment. In this and other embodiments, the chamber 12 is shown having a rectanguloid configuration by example only, but may have any suitable configuration for accommodating a work-piece. The diffuse reflective baffle 30 comprises a diffuse reflective material, such as, and not limited to, a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate.

Figure 3B:
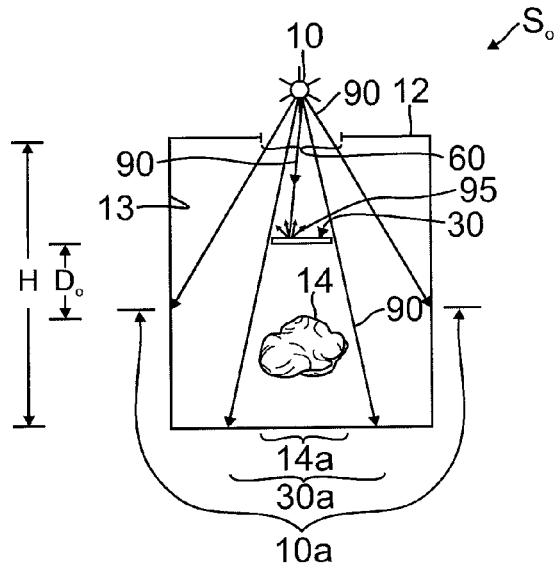
FIG. 3B is a cross-sectional view schematic diagram of the integrating optical system, as shown in FIG. 3A, comprising an integrating chamber, a light source, a diffuse reflective baffle disposed within the chamber and between the light source and a work-piece, the work-piece disposed within the chamber, in accordance with an embodiment.

Referring next to FIG. 3B, this schematic diagram illustrates a cross-sectional view of an integrating optical system $S_O$, as shown in FIG. 3A and taken at plane Z-Z, comprising an integrating chamber or a chamber 12, the chamber 12 having an input port 60 and a diffusely reflecting interior surface 13, a light source 10 disposed outside the chamber 12, a diffuse reflective baffle 30 disposed within the chamber 12 and between the light source 10 and a work-piece, such as a treatable target 14, disposed inside the chamber 12, wherein the incident light-rays 90, originate from the light source 10, enter the chamber 12, are blocked by the diffuse reflective baffle 30, wherein light is diffusely reflected from the diffusely reflecting interior surface 13 of the chamber 12, wherein some light-rays 95 are diffusely reflected by the diffuse reflective baffle 30 and then onto the interior surface of the chamber 12 or out of the chamber 12 through the input port 60, wherein some of the diffusely reflected light is incident upon the treatable target 14, whereby the treatable target 14 is treated to some extent by the diffusely reflected light. The light source 10 comprises a light-source field-of-view 10a of the inside of the chamber 12, as indicated by the corresponding bracket representation. The diffuse reflective baffle 30 casts a shadow 30a due to direct light-rays from the light source 10, as indicated by the corresponding bracket, on a wall of the chamber 12 such that a portion of the chamber wall is not in the light source's field-of-view due to the presence of the diffuse reflective baffle 30. The treatable target 14 would cast a shadow 14a, as indicated by the corresponding bracket, on a wall of the chamber 12 in the absence of a diffuse reflective baffle 30. For a treatable target 14 disposed inside the chamber 12, the diffuse reflective baffle 30 limits the light source's field-of-view of the treatable target 14 as well as the target's field-of-view of the light source 10. The distance $D_O$ between the diffuse reflective baffle 30 and the treatable target 14 comprises a value that is practicable for allowing sufficient room in the chamber 12 to optimize divergence of rays from the diffuse reflective baffle 30 prior to their incidence on the treatable target 14. Similarly, the distance between the diffuse reflective baffle 30 and the input port 60 is a value that is practicable for balancing chamber size, divergence of rays from diffuse reflective baffle 30, and light exiting the input port 60. The chamber 12 of this embodiment comprises a total height H.

Figure 3C:
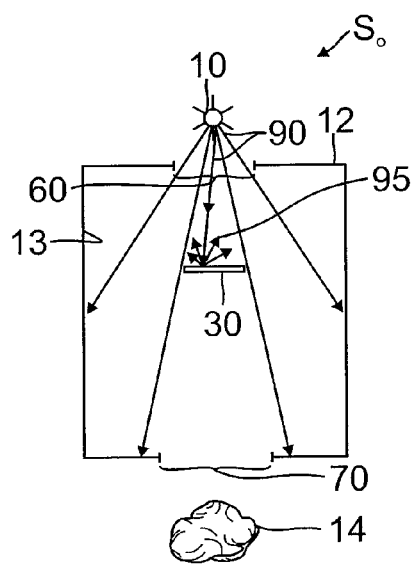
FIG. 3C is an interior view schematic diagram of an integrating optical system, comprising an integrating chamber, a light source disposed outside the chamber, a diffuse reflective baffle disposed within the chamber and between the light source and a work-piece, the work-piece disposed outside the chamber, in accordance with another embodiment.

Referring next to FIG. 3C, this interior view schematic diagram illustrates an integrating optical system $S_O$, comprising an integrating chamber or a chamber 12, the chamber 12 having an input port 60, an output port 70, and a diffusely reflecting interior surface 13, a light source 10 disposed outside the chamber 12, a diffuse reflective baffle 30 disposed within the chamber 12 and between the light source 10 and a work-piece, such as a treatable target 14, disposed outside the chamber 12, wherein some light is diffusely reflected from the interior surface of the chamber 12, wherein light is diffusely reflected by the diffuse reflective baffle 30 and then onto the diffusely reflecting interior surface 13 of the chamber 12, wherein some light-rays 95 are diffusely reflected by the diffuse reflective baffle 30 and then onto the diffusely reflecting interior surface 13 of the chamber 12 or out of the chamber 12 through input port 60, whereby some diffusely reflected light is provided and travels through the output port 70, wherein this diffusely reflected light is incident upon the treatable target 14, whereby the treatable target 14 is treated to some extent by the diffusely reflected light, in accordance with an embodiment. For a treatable target 14 disposed outside the chamber 12, the diffuse reflective baffle 30 limits the light source's field-of-view of the output port 70 such that no direct rays from the light source 10 exit the output port 70 without first being diffused by the diffuse reflective baffle 30.

Figure 4A:
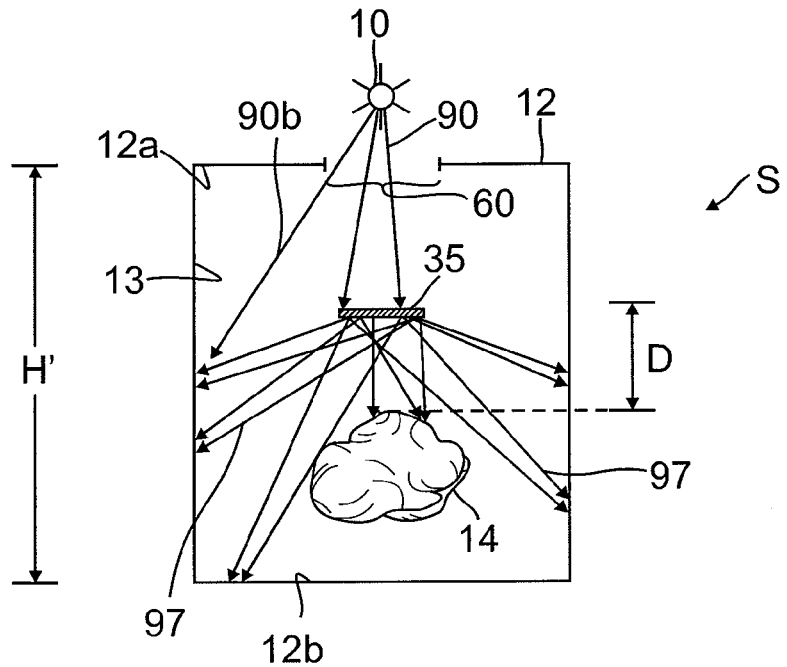
FIG. 4A is an interior view schematic diagram of an integrating optical system, comprising an integrating chamber, a light source disposed outside the chamber, a diffuse transmissive baffle disposed within the chamber and between the light source and a work-piece, the work-piece disposed inside the chamber, in accordance with one embodiment of the present invention.

Referring next to FIG. 4A, this interior view schematic diagram illustrates an integrating optical system S, comprising an integrating chamber or a chamber 12, the chamber 12 having an input port 60 and a diffusely reflecting interior surface 13, a light source 10 disposed outside the chamber 12, a diffuse transmissive baffle 35 disposed within the chamber 12 and in an optical path between the light source 10 and a work-piece, such as a treatable target 14 disposed inside the chamber 12, wherein light is diffusely reflected from the diffusely reflecting interior surface 13 of the chamber 12, and wherein light is diffusely transmitted by the diffuse transmissive baffle 35, whereby the treatable target 14 is generally uniformly treated by the diffusely reflected and transmitted light in a manner, such as curing, artificially weathering, disinfecting, and the like, by example only, in accordance with an embodiment of the present invention. It is noted that in this embodiment, there is no non-transmissive baffle or reflective baffle 30 positioned between the transmissive baffle 35 and the treatable target 14.

Still referring to FIG. 4A, light, comprising at least one light-ray 90b, originates from the light source 10, enters the chamber 12, impinges on the diffusely reflecting interior surface 13 of the chamber 12, wherein it is diffusely reflected from the diffusely reflecting interior surface 13 of the chamber 12 at least once before impinging other surfaces inside the chamber 12 including the treatable target 14. Furthermore, in the integrating optical system S, light, comprising at least one light-ray 90, originates from the light source 10, enters the chamber 12, and impinges on the diffuse transmissive baffle 35, wherein it is diffusely transmitted from the diffuse transmitting baffle 35 before impinging on other surfaces inside the chamber 12 including the treatable target 14.

Still referring to FIG. 4A, the treatable target 14 is disposed at a distance D from the diffuse transmissive baffle 35. The diffuse transmissive baffle facilitates passage of light from the light source therethrough in a diffuse manner. The distance D is generally chosen so that less than 50%, and preferably less than 25%, and in some cases less than 20%, and in further cases, less than 15% of the light, exiting the surface of diffuse transmissive baffle 35 and facing the treatable target 14, is initially incident on the treatable target 14 in order to allow sufficient light, exiting the diffuse transmissive baffle 35, to impinge directly on the diffusely reflecting surfaces 13 of chamber 12 and provide substantially uniform illumination of the entire treatable target 14. As such, in some embodiments, the distance D is generally chosen so that more than 50%, and preferably more than 75%, and in some cases more than 80%, and in further cases, more than 85% of the light, exiting the surface of diffuse transmissive baffle 35 and facing the treatable target 14, is initially incident on the diffusely reflecting surfaces 13 of the chamber 12 to provide substantially uniform illumination of the treatable target 14.

Still referring to FIG. 4A, the chamber 12 comprises a proximal wall 12a and a distal wall 12b separated by a distance H' that is set relative to the input port 60. The distance H', in combination with other dimensions of the chamber 12 not shown, is generally chosen so the total of all light loss surface areas of the chamber, including absorbing surfaces such as the treatable target 14 and open areas such as the input port 60, is less than 20% of the total enclosed surface area of chamber 12 and preferably less than 5% of the total surface area.

Figure 4B:
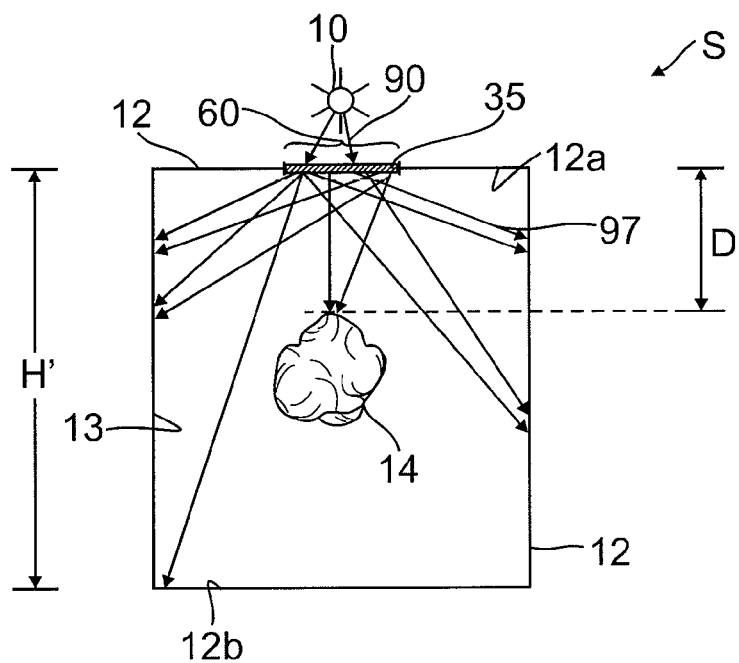
FIG. 4B is an interior view schematic diagram of an integrating optical system, comprising an integrating chamber, a light source disposed outside the chamber, a diffuse transmissive baffle disposed in an input port as well as between the light source and a work-piece, the work-piece disposed inside the chamber, in accordance with a further embodiment of the present invention.

Referring next to FIG. 4B, this interior view schematic diagram illustrates an integrating optical system S, comprising an integrating chamber or a chamber 12, the chamber 12 having an input port 60 and a diffusely reflecting interior surface 13, a light source 10 disposed outside the chamber 12, a diffuse transmissive baffle 35 disposed in the input port 60 and in an optical path between the light source 10 and a work-piece, such as a treatable target 14 disposed inside the chamber 12, wherein light is diffusely reflected from the diffusely reflecting interior surface 13 of the chamber 12, and wherein light is diffusely transmitted by the diffuse transmissive baffle 35, whereby the treatable target 14 is generally uniformly treated by the diffusely reflected and transmitted light in a manner, such as curing, artificially weathering, disinfecting, and the like, by example only, in accordance with an embodiment of the present invention. It is noted that in this embodiment, there is no non-transmissive baffle or reflective baffle 30 positioned between the transmissive baffle 35 and the treatable target 14.

Still referring to FIG. 4B, in the integrating optical system S, light, comprising at least one light-ray 90, originates from the light source 10 and is diffusely transmitted through the diffuse transmissive baffle 35 into the chamber 12. A light-ray 97 exiting the diffuse transmissive baffle 35 may impinge on the interior surface of the chamber 12, wherein it is diffusely reflected from the interior surface of the chamber 12 at least once before impinging other surfaces inside the chamber 12 including the treatable target 14. Furthermore, the light-ray 97 exiting the diffuse transmissive baffle 35 may impinge directly on the treatable target 14.

Still referring to FIG. 4B, the treatable target 14 is disposed at a distance D from the input port. The distance D is generally chosen so that less than 50%, and preferably less than 25%, and in some cases less than 20%, and in further cases, less than 15% of the light exiting the diffuse transmissive baffle 35 surface facing the treatable target 14 is initially incident on the treatable target 14, in order to allow sufficient light exiting the diffuse transmissive baffle 35 to impinge directly on the reflective surfaces of chamber 12 and provide substantially uniform illumination of the entire treatable target 14. As such, in some embodiments, the distance D is generally chosen so that more than 50%, and preferably more than 75%, and in some cases more than 80%, and in further cases, more than 85% of the light, exiting the diffuse transmissive baffle 35 surface facing the treatable target 14, is initially incident on the diffusely reflecting surfaces 13 of the chamber 12 to provide substantially uniform illumination of the treatable target 14.

Still referring to FIG. 4B, the chamber 12 comprises a proximal wall 12a and a distal wall 12b separated by a distance H' that is set relative to the input port 60. The distance H', in combination with other dimensions (not shown) of the chamber 12, is generally chosen so the total of all light loss surface areas of the chamber, including absorbing surfaces such as the treatable target 14 and open areas such as the input port 60, is less than 20% of the total enclosed surface area of chamber 12 and preferably less than 5% of the total surface area.

Figure 4C:
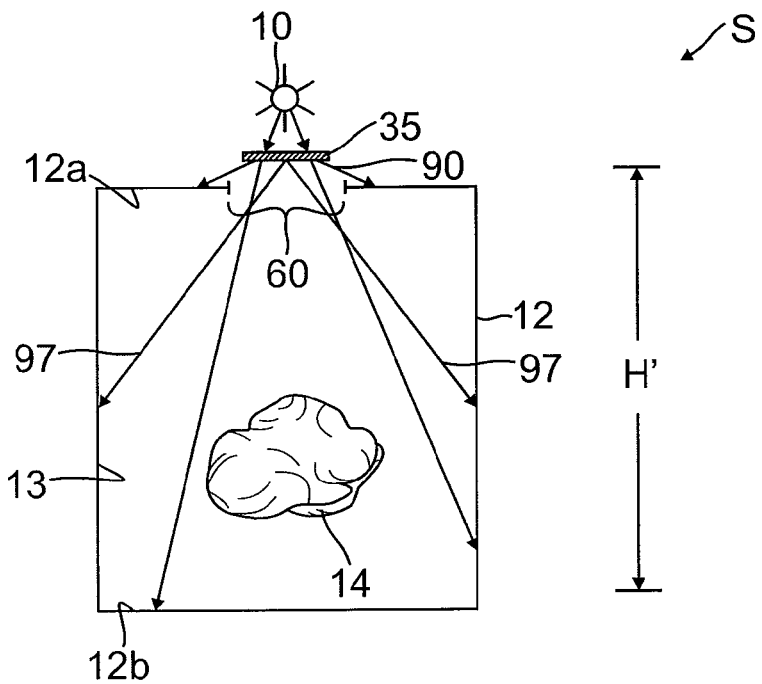
FIG. 4C is an interior view schematic diagram of an integrating optical system, comprising an integrating chamber, a light source disposed outside the chamber, a diffuse transmissive baffle disposed outside the chamber and between the light source and a work-piece, the work-piece disposed inside the chamber, in accordance with a further embodiment of the present invention.

Referring next to FIG. 4C, this interior view schematic diagram illustrates an integrating optical system S, comprising an integrating chamber or a chamber 12, the chamber 12 having an input port 60 and a diffusely reflecting interior surface 13, a light source 10 disposed outside the chamber 12, a diffuse transmissive baffle 35 disposed outside the chamber 12 and in an optical path between the light source 10 and a work-piece, such as a treatable target 14 disposed inside the chamber 12, wherein light is diffusely reflected from the diffusely reflecting interior surface 13 of the chamber 12, and wherein light is diffusely transmitted by the diffuse transmissive baffle 35, whereby the treatable target 14 is generally uniformly treated by the diffusely reflected and transmitted light in a manner, such as curing, artificially weathering, disinfecting, and the like, by example only, in accordance with an embodiment of the present invention.

Still referring to FIG. 4C, the integrating optical system S of FIG. 4C, light, comprising at least one light-ray 90, originates from the light source 10 and is diffusely transmitted thru the diffuse transmissive baffle 35 into the chamber 12. At least one ray of light 97, exiting the diffuse transmissive baffle 35, impinges on the diffusely reflecting interior surfaces 13 of the chamber 12, wherein it is diffusely reflected from the interior surface of the chamber 12 at least once before impinging other surfaces inside the chamber 12 including the treatable target 14. Furthermore, light exiting the diffuse transmissive baffle 35 may impinge directly on the treatable target 14.

Still referring to FIG. 4C, the chamber 12 comprises a proximal wall 12a and a distal wall 12b separated by a distance H that is set relative to the input port 60. The distance H', in combination with other dimensions (not shown) of the chamber 12, is generally chosen so the total of all light loss surface areas of the chamber, including absorbing surfaces such as the treatable target 14, and open areas, such as the input port 60, is less than 20% of the total enclosed surface area of chamber 12 and preferably less than 5% of the total surface area.

Still referring to FIG. 4C and referring back to FIG. 4B, the chamber 12 may be fabricated in a size that is significantly smaller than the chambers of the same effectiveness, that are built in accordance with the embodiments shown in FIGS. 3A-3C, by incorporating the diffuse transmissive baffle 35 either at the input port 60 or outside the chamber 12. For example, in FIG. 4B, the distance (not shown) between the input port 60 and the diffuse transmissive baffle 35 is approximately zero; and, thus, the total height H' of the chamber 12 is less than the total height H shown in FIG. 3B. Similarly, the total height H' of the chamber 12, as shown in FIG. 4C, is less than the total height H as shown in FIG. 3B. Thus, the diffuse transmissive baffle 35 allows for smaller chamber designs in some embodiments of the present invention than in the embodiments shown in FIGS. 3A-3C, thereby reducing cost and power requirements while achieving substantially the same performance.

Referring back to FIGS. 4A-4C, some light-rays of the light-rays 90 may not enter the chamber 12. For Lambertian light sources, such as arc lamps, not all rays emanating from the light source 10 can enter the chamber 12. Some rays that are incident on the diffuse transmissive baffle 35 are also reflected away from the input port 60 as first surface reflections. Some rays reflected by the diffusely reflecting interior surfaces 13 of the chamber 12 will exit the input port 60 and never return thereto. As such, including a secondary reflecting chamber, e.g., an auxiliary chamber 22 is beneficial in some embodiments of the present invention as shown in FIG. 5A, and described, infra.

Figure 5A:
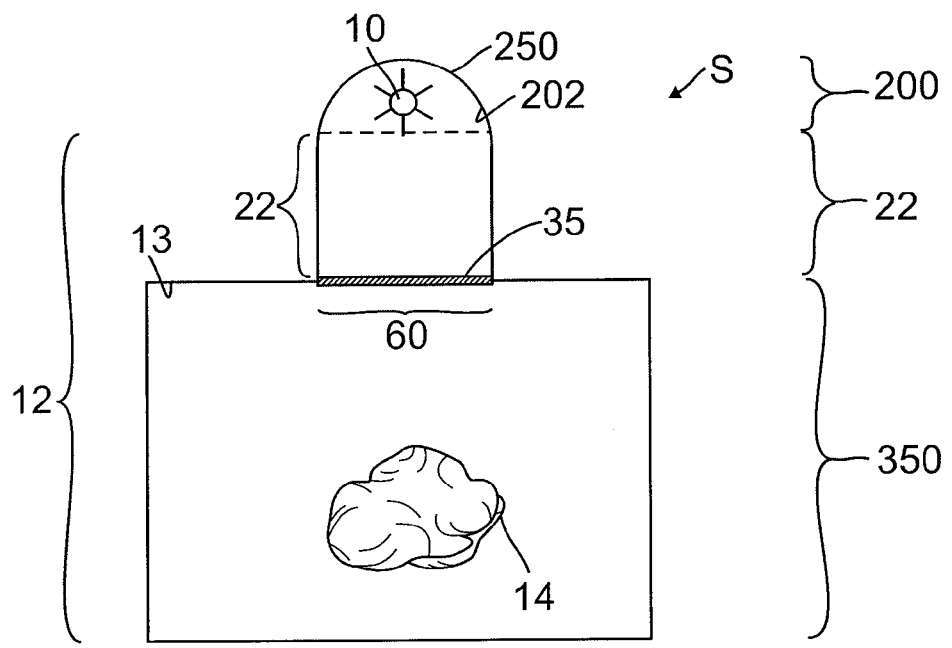
FIG. 5A is an interior view schematic diagram of an integrating optical system, comprising a chamber having a main chamber and an auxiliary chamber, a lamp assembly disposed adjacent the auxiliary chamber, a light source disposed inside the lamp assembly, a diffuse transmissive baffle disposed in the input port and between the light source and a work-piece, the work-piece disposed inside the chamber, in accordance with a further embodiment of the present invention.

Referring next to FIG. 5A, this interior view schematic diagram illustrates an integrating optical system S, comprising a chamber 12, the chamber 12 comprising a main chamber 350 and an auxiliary chamber 22, the main chamber 350 having an input port 60 and a diffusely reflecting interior surface 13, the auxiliary chamber 22 being disposed adjacent the main chamber 350, a lamp assembly 200 disposed adjacent the auxiliary chamber 22, a light source 10 disposed inside the lamp assembly 200, a diffuse transmissive baffle 35 disposed in the input port 60 and in an optical path between the light source 10 and a work-piece, such as a treatable target 14, disposed inside the chamber 12, wherein light originates from the light source 10 and enters the auxiliary chamber 22.

The interior surface of the auxiliary chamber 22 may or may not be reflective. If it is reflective, it may or may not be diffuse reflective. Preferably, the interior surface of auxiliary chamber 22 is diffuse reflective. Light impinging on the diffuse transmissive baffle 35 is diffusely transmitted and enters the main chamber 350. Light entering the main chamber 350 impinges on the diffusely reflecting interior surface 13 of the chamber 12 as well as on the treatable target 14. Light impinging on the diffusely reflecting interior surface 13 of the main chamber 350 is diffusely reflected. The combination of diffusely transmitted light from the diffuse transmissive baffle 35 and diffusely reflected light from the diffusely reflecting interior surface 13 of the main chamber 350 generally uniformly treats the treatable target 14 in a manner, such as curing, artificially weathering, disinfecting, and the like, by example only, in accordance with an embodiment of the present invention. The lamp assembly 200 comprises a light reflector 250 for enhancing reflection of light from the light source 10 toward the auxiliary chamber 22. The light reflector 250 comprises a highly reflective interior surface, such as a diffuse reflective interior surface 202. The highly reflective interior surface comprises a material, such as a highly reflective specular reflector, a highly reflective diffuse reflector, a highly polished conductive material, a polished aluminum, a dielectric material, a substrate with a surface coating that allows selective wavelengths to be reflected and others to be either transmitted or absorbed by the substrate, a diffuse reflective material, such as, and not limited to, a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate. The light reflector 250 may be focusing (elliptical in cross-section), and, thus, specularly reflecting, or the light reflector 250 may be diffusely reflecting. Further, the light reflector 250 may have surface features, such as dimples or bumps. Alternatively, the light reflector 250 can have either a diffuse reflective surface or a specular reflective surface. Also, the light source 10 can be located relative to the light reflector 250 so that its radiation is either focused or not focused by the light reflector 250, e.g., the lamp assembly comprises a focus characteristic, such as being in-focus and out-of-focus.

Figure 5B:
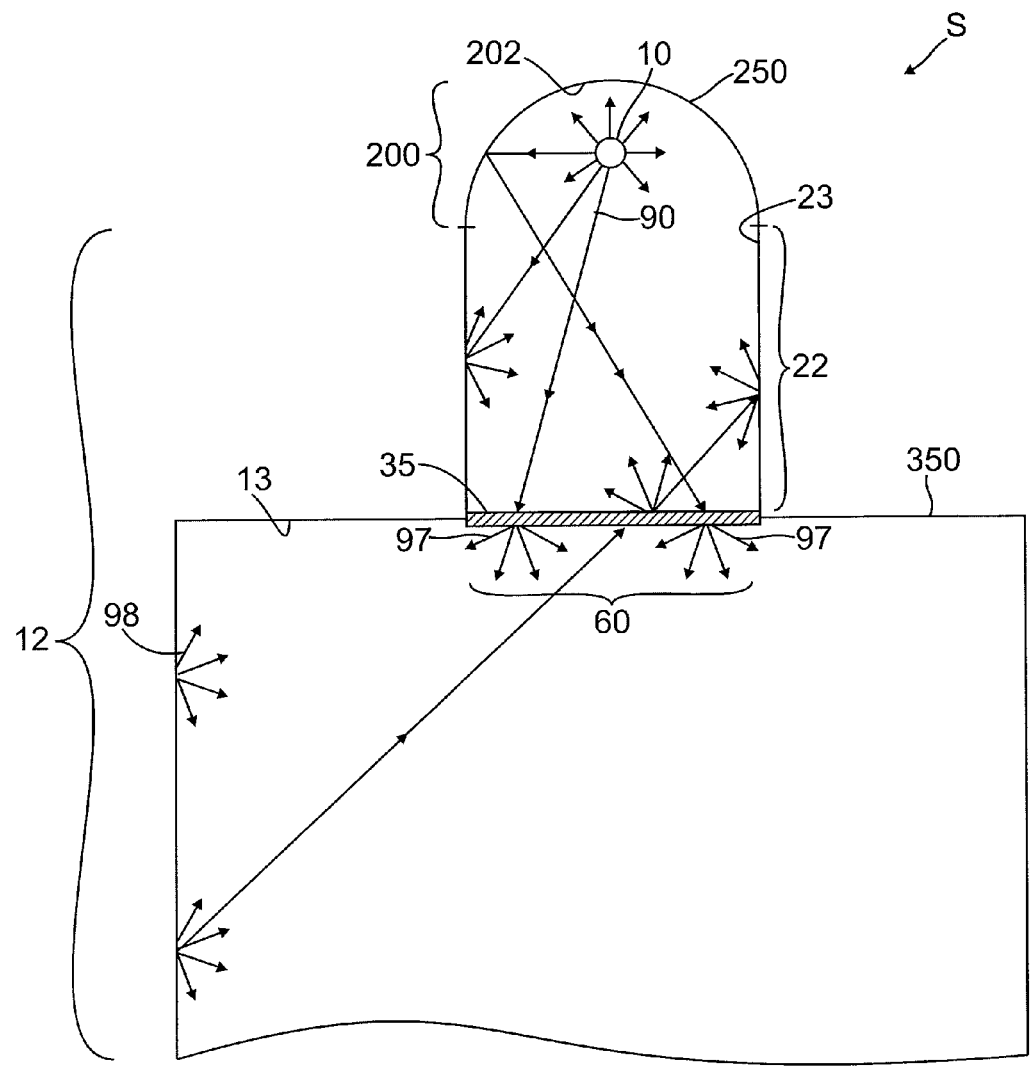
FIG. 5B is an interior cut-away view schematic diagram of an integrating optical system, comprising a chamber having a main chamber and an auxiliary chamber, a lamp assembly disposed adjacent the auxiliary chamber, a light source disposed inside the lamp assembly, a diffuse transmissive baffle disposed in an input port and between the light source and a work-piece, the work-piece disposed inside the chamber, in accordance with a further embodiment of the present invention.

Referring to FIG. 5B, this interior cut-away view schematic diagram illustrates an integrating optical system S, comprising a chamber 12, the chamber 12 comprising a main chamber 350 and an auxiliary chamber 22, the main chamber 350 having an input port 60 and a diffusely reflecting interior surface 13, the auxiliary chamber 22 being disposed adjacent the main chamber 350, a lamp assembly 200 disposed adjacent the auxiliary chamber 22, a light source 10 disposed inside the lamp assembly 200, a diffuse transmissive baffle 35 disposed in the input port 60 and in an optical path between the light source 10 and a work-piece, such as a treatable target 14 (FIG. 5A) is disposed inside the chamber 12, wherein light, comprising at least one light-ray 90, originates from the light source 10 and enters the auxiliary chamber 22. The interior surface 23 of the auxiliary chamber 22 may or may not be reflective; and, if the interior surface 23 is reflective, the interior surface 23 may or may not be diffuse reflective. Preferably, the interior surface 23 of the auxiliary chamber 22 is diffuse reflective. Light impinging on the diffuse transmissive baffle 35 is diffusely transmitted and enters the main chamber 350 as at least one diffusely transmitted light-ray 97, impinges on the diffusely reflecting interior surface 13 of the main chamber 350, wherein light is diffusely reflected from the interior surface of the main chamber 350 as at least one light-ray 98 being diffusely reflected from a diffusely reflecting interior surface 13 of the main chamber 350, whereby a diffusely reflected light is provided, wherein the diffusely reflected light is substantially uniformly incident upon the treatable target 14 (FIG. 5A), whereby the treatable target 14 (FIG. 5A) is substantially uniformly treated by the diffusely reflected, and the diffusely transmitted light, inside the main chamber 350 in a manner, such as curing, artificially weathering, disinfecting, and the like, by example only, in accordance with an embodiment of the present invention. The lamp assembly 200 comprises a lamp or light reflector 250 for enhancing reflection of light from the light source 10 toward the auxiliary chamber 22. The interior surface 23 of the auxiliary chamber 22 may also comprise a specular or diffuse reflective interior surface and is preferably diffuse reflective. The specular or diffuse reflective interior surface comprises a material, such as a highly reflective specular reflector, a highly reflective diffuse reflector, a highly polished conductive material, a polished aluminum, a dielectric material, a dielectric substrate, a conductive substrate with a surface coating that allows selective wavelengths to be reflected and others to be either transmitted or absorbed by the substrate, a diffuse reflective material, such as, and not limited to, a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate. The light reflector 250 comprises a highly reflective interior surface, such as a diffuse reflective interior surface 202. The highly reflective interior surface comprises a material, such as a highly reflective specular reflector, a highly reflective diffuse reflector, a highly polished conductive material, a polished aluminum, a dielectric material, a substrate with a surface coating that allows selective wavelengths to be reflected and others to be either transmitted or absorbed by the substrate, a diffuse reflective material, such as, and not limited to, a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate. The light source 10 may comprise a lighting element, such as a discharge lamp, a microwave-excited arc lamp, an electrodeless arc lamp, a low pressure arc lamp, a medium pressure arc lamp, a high pressure arc lamp, an incandescent lamp, a light emitting diode, and a laser. Further, the light reflector 250 may have surface features, such as dimples or bumps. Alternatively, the light reflector 250 can have either a diffuse reflective surface or a specular reflective surface. Also, the light source 10 can be located relative to the light reflector 250 so that its radiation is either focused or not focused by the light reflector 250.

Referring generally to FIGS. 6A-9B, as described, infra, these experimental embodiments demonstrate that the diffuse transmitting baffle 35 is at least as effective as a diffuse reflective baffle 30 in providing generally uniform irradiance within the chamber 12. In larger chambers, wherein the diffuse reflective baffle 30 would be larger and the diffuse transmitting baffle 35 would remain unchanged, and where the total enclosed chamber surface area would be smaller using the diffuse transmissive baffle 35 than using a diffuse reflective baffle 30, the irradiance is expected to be higher within the chamber 12 as the irradiance within the chamber 12 is inversely proportional to reflecting surface area, e.g., the sum of the interior surface of the chamber 12 and the reflecting surface area of the diffuse reflective baffle 30. As such, the chamber reflecting surface area increases as the chamber volume increases. With a diffuse reflective baffle 30, additional surface area is added by adding volume to the chamber 12 for accommodating the diffuse reflective baffle 30 and by the surface area of the diffuse reflective baffle 30 itself. However, by using a diffuse transmissive baffle 35, the increasing reflecting area will be relatively less as the chamber size increases due to the absence of the diffuse reflective baffle 30.

Figure 6A:
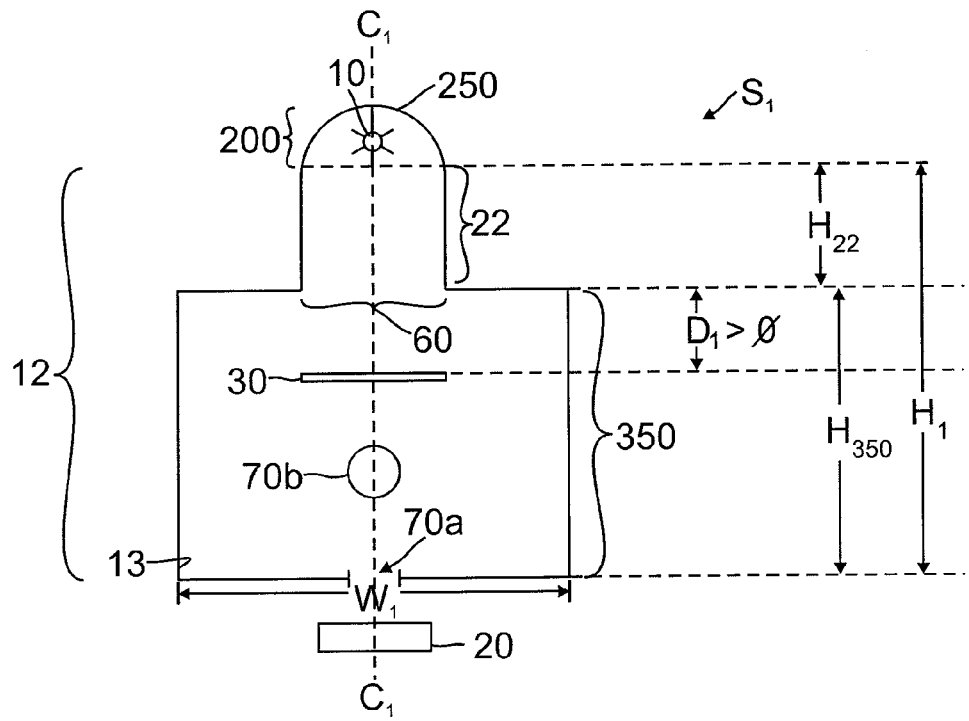
FIG. 6A is an interior view schematic diagram of an integrating optical system, having a centerline and comprising a chamber having a main chamber and an auxiliary chamber, a lamp assembly coupled with the auxiliary chamber, a light source disposed inside the lamp assembly, a diffuse reflective baffle disposed inside the main chamber and between the light source and a bottom output port, a detector disposed outside the chamber and at the bottom output port, and a detector disposed outside the chamber and at a side output port, in accordance with an embodiment.

Referring next to FIG. 6A, this interior view schematic diagram illustrates an integrating optical system $S_1$, having a centerline $C_1$-$C_1$ and comprising a chamber 12, the chamber 12 comprising a main chamber 350 and an auxiliary chamber 22, the main chamber 350 having an input port 60, a bottom output port 70a and a side output port 70b, and a diffusely reflecting interior surface 13, the auxiliary chamber 22 coupled with the main chamber 350, a lamp assembly 200 coupled with the auxiliary chamber 22, a light source 10 disposed inside the lamp assembly 200, a diffuse reflective baffle 30 disposed inside the main chamber 350 and between the light source 10 and the bottom output port 70a, a detector 20 disposed outside the chamber 12 and at the bottom output port 70a, and a detector 20 (not shown) disposed outside the chamber 12 and at the side output port 70b, wherein the diffuse reflective baffle 30 comprises a width that is less than that of the main chamber 350, wherein light originates from the light source 10, enters the auxiliary chamber 22, impinges on the diffuse reflective baffle 30 and the diffusely reflecting interior surface 13, is diffusely reflected, impinges on the diffusely reflecting interior surface 13 of the main chamber 350, wherein light is diffusely reflected from the diffusely reflecting interior surface 13 of the main chamber 350, wherein light is not entirely reflected back toward the light source 10, whereby a diffusely reflected light is provided, and wherein the diffusely reflected light impinges on the detector 20 and may be then measurable by the detector 20, in accordance with an embodiment. The lamp assembly 200 comprises a light reflector 250 for enhancing reflection of light from the light source 10 toward the auxiliary chamber 22. The light source 10 comprises a lighting element, such as one or more of a discharge lamp, a microwave-excited arc lamp, an electrodeless arc lamp, a low pressure arc lamp, a medium pressure arc lamp, a high pressure arc lamp, an incandescent lamp, a light emitting diode, and a laser. For example, in this embodiment, the main chamber 350 comprises a height $H_{350}$ of approximately 12 inches, a length $L_1$ of approximately 12 inches (FIG. 6B), and a width $W_1$ of approximately 12 inches, wherein the diffuse reflective baffle 30 is disposed at a distance $D_1$ of approximately 4 inches from the input port 60. The auxiliary chamber height $H_{22}$ is as shown in this figure. The total height of the chamber 12 can be expressed as $H_1=H_{350}+H_{22}$. Experimentally, as measured by the detector 20 (bottom) and the side detector (not shown), the bottom output port 70a has an exitance of approximately 0.24 W/cm$^2$ while the side output port 70b has an exitance of approximately 0.23 W/cm$^2$ by using this embodiment. This embodiment demonstrates that the irradiance within the chamber 12 is fairly uniform, because the exitance value of the bottom output port 70a and the exitance value of the side output port 70b are within 5% of one another.

Figure 6B:
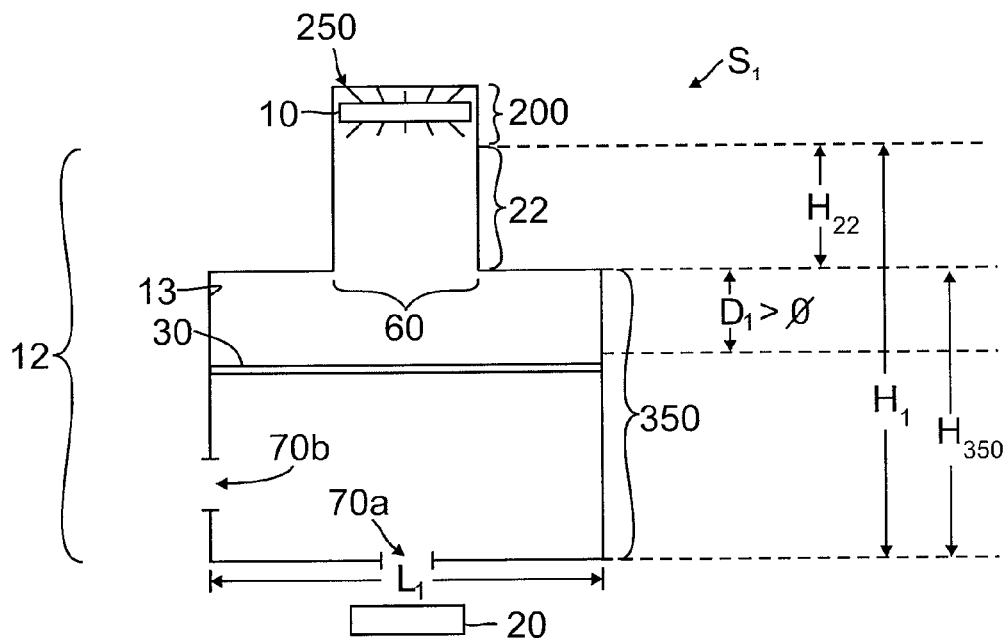
FIG. 6B is a cross-sectional view schematic diagram of the embodiment of the integrating optical system of FIG. 6A, taken along a centerline of FIG. 6A.

Referring to FIG. 6B, this cross-sectional view schematic diagram of the integrating optical system, as shown in FIG. 6A and taken along a centerline $C_1$-$C_1$, illustrates an integrating optical system $S_1$, comprising a chamber 12, the chamber 12 comprising a main chamber 350 and an auxiliary chamber 22, the main chamber 350 having an input port 60, a bottom output port 70a and a side output port 70b, and a diffusely reflecting interior surface 13, the auxiliary chamber 22 being coupled with the main chamber 350, a lamp assembly 200 being coupled with the auxiliary chamber 22, a light source 10 disposed inside the lamp assembly 200, a diffuse reflective baffle 30 disposed inside the main chamber 350 and between the light source 10 and the bottom output port 70a, a detector 20 disposed outside the chamber 12 and at the bottom output port 70a, and a detector 20 (not shown) disposed outside the chamber 12 and at the side output port 70b, wherein the diffuse reflective baffle 30 comprises a width that is less than that of the main chamber 350, wherein light originates from the light source 10, enters the auxiliary chamber 22, impinges on the diffuse reflective baffle 30 and the diffusely reflecting interior surface 13, is diffusely reflected, impinges on the diffusely reflecting interior surface 13 of the main chamber 350, wherein light is diffusely reflected from the diffusely reflecting interior surface 13 of the main chamber 350, wherein light is not entirely reflected back toward the light source 10, whereby a diffusely reflected light is provided, and wherein the diffusely reflected light impinges on the detector 20 and may be then measurable by the detector 20, in accordance with an embodiment. The lamp assembly 200 comprises a light reflector 250 for enhancing reflection of light from the light source 10 toward the auxiliary chamber 22. The light source 10 comprises a lighting element, such as a discharge lamp, a microwave-excited arc lamp, an electrodeless arc lamp, a low pressure arc lamp, a medium pressure arc lamp, a high pressure arc lamp, an incandescent lamp, a light emitting diode, and a laser. For example, in this embodiment, the main chamber 350 comprises a height $H_{350}$ of approximately 12 inches, a length $L_1$ of approximately 12 inches, and a width $W_1$ of approximately 12 inches (FIG. 6A), wherein the diffuse reflective baffle 30 is disposed at a distance $D_1$ of approximately 4 inches from the input port 60. The auxiliary chamber height $H_{22}$ is as shown in the figure. The total height of the chamber 12 can be expressed as $H_1=H_{350}+H_{22}$. Experimentally, the bottom output port 70a has an exitance of approximately 0.24 W/cm$^2$ while the side output port 70b has an exitance of approximately 0.23 W/cm$^2$ by using this embodiment. This embodiment demonstrates that the irradiance within the chamber 12 is fairly uniform, because the exitance value of the bottom output port 70a and the exitance value of the side output port 70b are within 5% of one another.

Figure 7A:
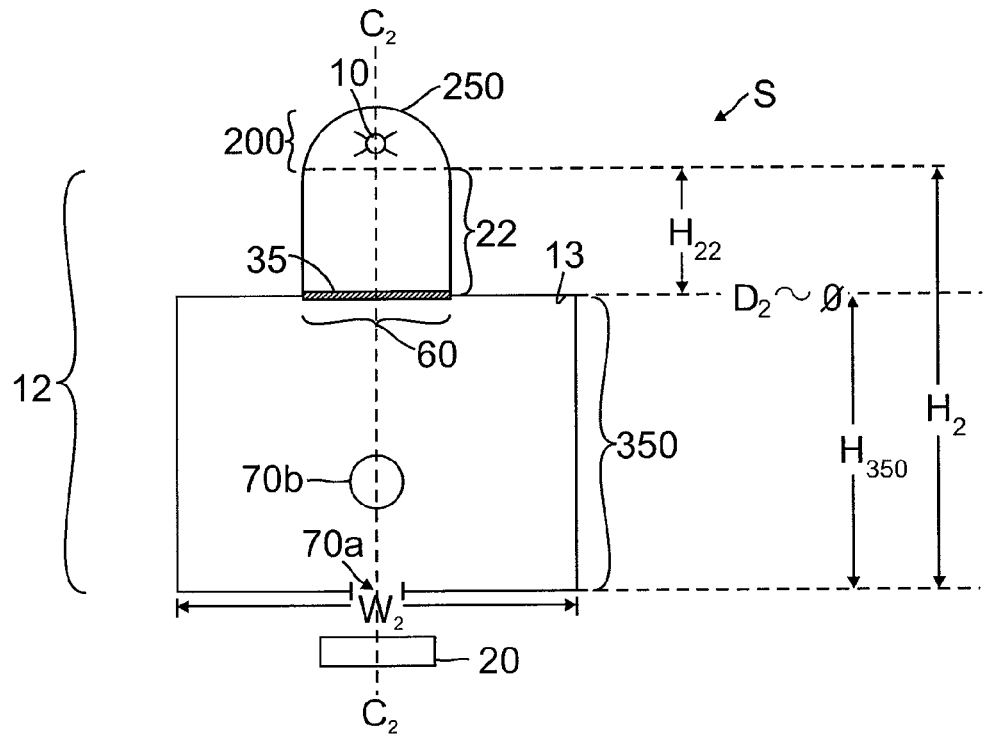
FIG. 7A is an interior view schematic diagram of an integrating optical system, having a centerline and comprising a chamber having a main chamber and an auxiliary chamber, a lamp assembly coupled with the auxiliary chamber, a light source disposed outside the chamber but inside the lamp assembly, a diffuse transmissive baffle disposed at an input port and between the light source and a bottom output port, a detector disposed outside the chamber and at the bottom output port, and another detector disposed outside the chamber and at the side output port, in accordance with a further embodiment of the present invention.

Referring next to FIG. 7A, this interior view schematic diagram illustrates an integrating optical system S, having a centerline $C_2$-$C_2$ and comprising a chamber 12, the chamber 12 comprising a main chamber 350 and an auxiliary chamber 22, the main chamber 350 having an input port 60, a bottom output port 70a and a side output port 70b, and a diffusely reflecting interior surface 13, the auxiliary chamber 22 being coupled with the main chamber 350, a lamp assembly 200 being coupled with the auxiliary chamber 22, a light source 10 disposed outside the chamber 12 but inside the lamp assembly 200, a diffuse transmissive baffle 35 disposed at the input port 60 and in an optical path between the light source 10 and the bottom output port 70a, a detector 20 disposed outside the chamber 12 and at the bottom output port 70a, and a detector 20 (not shown) disposed outside the chamber 12 and at the side output port 70b, wherein the diffuse transmissive baffle 35 comprises a width that is less than that of the main chamber 350, wherein light originates from the light source 10, enters the auxiliary chamber 22, impinges on the diffuse transmissive baffle 35, is diffusely transmitted, impinges on the diffusely reflecting interior surface 13 of the main chamber 350, wherein light is diffusely reflected from the diffusely reflecting interior surface 13 of the main chamber 350, wherein not all light is reflected back toward the light source 10, whereby a diffusely reflected light is provided, and wherein the diffusely reflected light impinges on the detector 20 and may be then measurable by the detector 20, in accordance with an embodiment of the present invention. The lamp assembly 200 comprises a light reflector 250 for enhancing reflection of light from the light source 10 toward the auxiliary chamber 22. The light source 10 comprises a lighting element, such as at least one of a discharge lamp, a microwave-excited arc lamp, an electrodeless arc lamp, a low pressure arc lamp, a medium pressure arc lamp, a high pressure arc lamp, an incandescent lamp, a light emitting diode, and a laser. For example, in this embodiment, the main chamber 350 comprises a height $H_{350}$ of approximately 12 inches, a length $L_2$ of approximately 12 inches (FIG. 7B), and a width $W_2$ of approximately 12 inches, wherein the diffuse reflective baffle 30 is disposed at a distance $D_2$ of approximately 0 inches from the input port 60. The auxiliary chamber height $H_{22}$ is as shown in the figure. The total height of the chamber 12 can be expressed as $H_2=H_{350}+H_{22}$. Experimentally, the bottom output port 70$a$ has an exitance of approximately 0.23 W/cm$^2$ while the side output port 70$b$ has an exitance of approximately 0.22 W/cm$^2$ by using this embodiment. This result demonstrates that use of a diffuse transmissive baffle 35 is at least as effective as use of a diffuse reflective baffle 30 (FIG. 6A) for providing largely uniform radiation within the chamber 12 and that the diffuse transmissive baffle 35 does not introduce excessive losses to the integrating optical system S, either by absorption or by back-reflection to the light reflector 250, since the measured irradiance of the system in FIG. 7A is approximately equal to the measured irradiance of the system of FIG. 6A.

Still referring to FIG. 7A, if the height $H_{350}$ of the main chamber 350 is set as being equal to the bottom-to-baffle distance of the chamber 12, relative to the embodiment of FIG. 6A, the bottom-to-baffle distance may be reduced (e.g., see the embodiment of FIGS. 7C and 7D) such that the exitance at the bottom output port 70$a$ and the side output port 70$b$ would be higher while maintaining uniformity and while allowing the same volume in the main chamber 350 for insertion of a treatable target 14. As more fully explained in relation to FIGS. 7C and 7D, this shows that the diffuse transmissive baffle 35 allows for smaller sized chambers than would be required when using the diffuse reflective baffle 30, resulting in greater irradiance while maintaining uniformity and treatment volume.

Figure 7B:
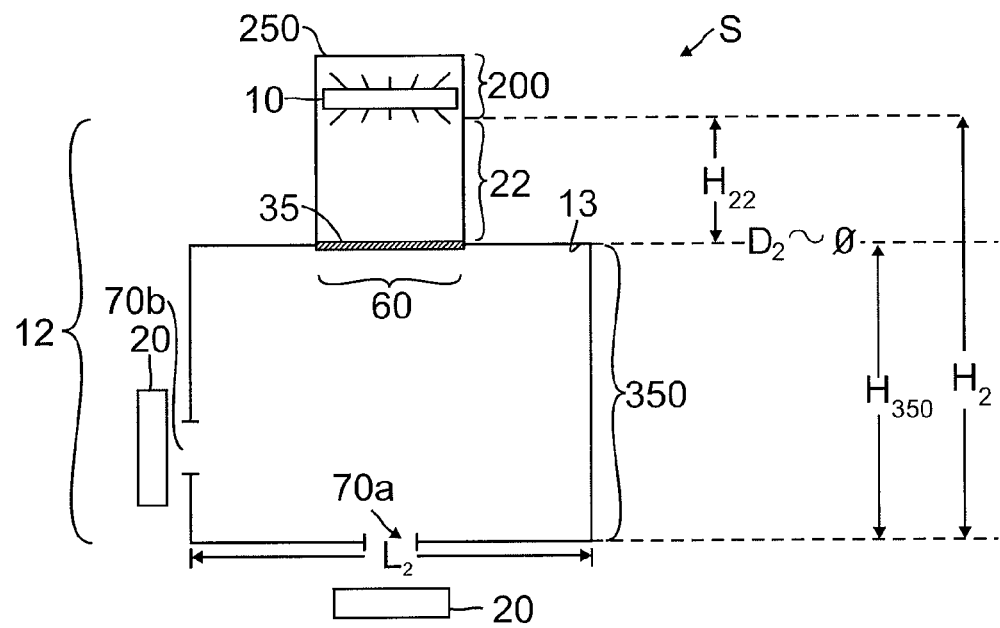
FIG. 7B is a cross-sectional view schematic diagram of the embodiment of the integrating optical system of FIG. 7B taken along a centerline of FIG. 7A.

Referring to FIG. 7B, this interior view schematic diagram illustrates an integrating optical system S, as shown in FIG. 7A and taken along the centerline $C_2$-$C_2$, comprising a chamber 12, the chamber 12 comprising a main chamber 350 and an auxiliary chamber 22, the main chamber 350 having an input port 60, a bottom output port 70$a$ and a side output port 70$b$, and a diffusely reflecting interior surface 13, the auxiliary chamber 22 being coupled with the main chamber 350, a lamp assembly 200 being coupled with the auxiliary chamber 22, a light source 10 disposed outside the chamber 12 but inside the lamp assembly 200, a diffuse transmissive baffle 35 disposed at the input port 60 and in an optical path between the light source 10 and the bottom output port 70$a$, a detector 20 disposed outside the chamber 12 and at the bottom output port 70$a$, and a detector 20 (not shown) disposed outside the chamber 12 and at the side output port 70$b$, wherein the diffuse transmissive baffle 35 comprises a width that is less than that of the main chamber 350, wherein light originates from the light source 10, enters the auxiliary chamber 22, impinges on the diffuse transmissive baffle 35, is diffusely transmitted, and impinges on the diffusely reflecting interior surface 13 of the main chamber 350, wherein light is diffusely reflected from the diffusely reflecting interior surface 13 of the main chamber 350, wherein light is not completely reflected back toward the light source 10, whereby a diffusely reflected light is provided, and wherein the diffusely reflected light impinges on the detector 20 and may be then measurable by the detector 20, in accordance with an embodiment of the present invention. The lamp assembly 200 comprises a light reflector 250 for enhancing reflection of light from the light source 10 toward the auxiliary chamber 22. The light source 10 comprises a lighting element, such as a discharge lamp, a microwave-excited arc lamp, an electrodeless arc lamp, a low pressure arc lamp, a medium pressure arc lamp, a high pressure arc lamp, an incandescent lamp, a light emitting diode, and a laser. For example, in this embodiment, the main chamber 350 comprises a height $H_{350}$ of approximately 12 inches, a length $L_2$ of approximately 12 inches, and a width $W_2$ of approximately 12 inches (FIG. 7A), wherein the diffuse reflective baffle 30 is disposed at a distance $D_2$ of approximately 0 inches from the input port 60. The auxiliary chamber height $H_{22}$ is as shown in the figure. The total height of the chamber 12 can be expressed as $H_2=H_{350}+H_{22}$. Experimentally, the bottom output port 70$a$ has an exitance of approximately 0.23 W/cm$^2$ while the side output port 70$b$ has an exitance of approximately 0.22 W/cm$^2$ by using this embodiment. This result demonstrates that use of a diffuse transmissive baffle 35 is at least as effective as use of a diffuse reflective baffle 30 (FIG. 6B) for providing largely uniform radiation within the chamber 12 and that the diffuse transmissive baffle 35 does not introduce excessive losses to the integrating optical system S, whether it be via absorption or back-reflection to the light reflector 250, since the measured irradiance of the system in FIG. 7B is approximately equal to the measured irradiance of the system of FIG. 6B.

Figure 7C:
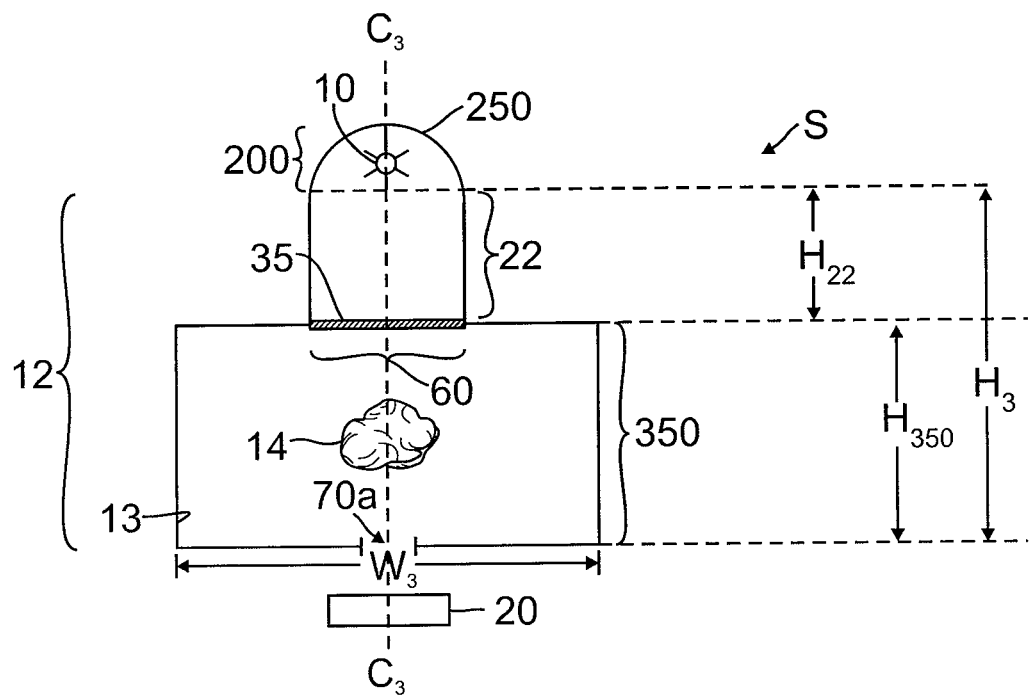
FIG. 7C is an interior view schematic diagram of an integrating optical system, having a centerline and comprising a chamber, a diffuse transmissive baffle disposed at an input port and between a light source and a bottom output port, a detector disposed outside the chamber and at the bottom output port, in accordance with a further embodiment of the present invention.

Referring next to FIG. 7C, this interior view schematic diagram illustrates an integrating optical system S, having a centerline C3-C3 and comprising a chamber 12, the chamber 12 comprising a main chamber 350 and an auxiliary chamber 22, the main chamber 350 having an input port 60, a bottom output port 70$a$, and a diffusely reflecting interior surface 13, the auxiliary chamber 22 being coupled with the main chamber 350, a lamp assembly 200 being coupled with the auxiliary chamber 22, a light source 10 disposed outside the chamber 12 but inside the lamp assembly 200, a diffuse transmissive baffle 35 disposed at the input port 60 and in an optical path between the light source 10 and the bottom output port 70$a$, a detector 20 disposed outside the chamber 12 and at the bottom output port 70$a$, and a detector 20 (not shown) disposed outside the chamber 12 and at the side output port 70$b$ (not shown), wherein the diffuse transmissive baffle 35 comprises a width that is less than that of the main chamber 350, wherein light originates from the light source 10, enters the auxiliary chamber 22, impinges on the diffuse transmissive baffle 35, is diffusely transmitted, impinges on the diffusely reflecting interior surface 13 of the main chamber 350, wherein light is diffusely reflected from the diffusely reflecting interior surface 13 of the main chamber 350, wherein not all light is reflected back toward the light source 10, whereby a diffusely reflected light is provided, and wherein the diffusely reflected light impinges on the detector 20 and may be then measurable by the detector 20, in accordance with an embodiment of the present invention. The lamp assembly 200 comprises a light reflector 250 for enhancing reflection of light from the light source 10 toward the auxiliary chamber 22. The light source 10 comprises a lighting element, such as at least one of a discharge lamp, a microwave-excited arc lamp, an electrodeless arc lamp, a low pressure arc lamp, a medium pressure arc lamp, a high pressure arc lamp, an incandescent lamp, a light emitting diode, and a laser. For example, in this embodiment, the main chamber 350 comprises a height H350 of approximately 8 inches, a length L3 of approximately 12 inches (FIG. 7D), and a width W3 of approximately 12 inches, wherein the diffuse transmissive baffle 35 is disposed at a distance D3 of approximately 0 inches from the input port 60. The auxiliary chamber height H22 is as shown in the figure. The total height of the chamber 12 can be expressed as H3=H350+H22. In particular, this embodiment allows for greater irradiance, e.g., an increase in irradiance of approximately 18%, while maintaining uniformity, and providing a treatment volume with smaller sizes, e.g., a main chamber 350 having a decrease in surface area of approximately 22% for treating a treatable target 14 having the same or comparable volume, than by using the diffuse reflective baffle 30. The decreased main chamber height H350 results in a main chamber volume reduction of approximately 33%. In some embodiments, a volume reduction in a range of up to approximately 90%, up to approximately 75%, up to approximately 50%, up to approximately 40%, and up to approximately 30% is possible, depending on the implementation, the geometry, the reflective surface area, the disposition of the treatable target 14, among other factors. Thus, in accordance with some embodiments, the use of a diffuse transmissive baffle will allow for integrating sphere chamber designs that provide increased irradiance with substantially the same or similar uniformity but with a decreased reflective surface area (resulting in a lower volume chamber) relative to designs using a diffuse reflective baffle (such as with the embodiment of FIGS. 6A and 6B). It is understood that the specific increases in irradiance and reductions in reflective surface area as well as changes in uniformity will depend on the specific implementation including dimensions, material selection and light characteristics and other variables, for example. It is further noted that in some embodiments, when comparing the embodiment of FIGS. 7C and 7D with the embodiment of FIGS. 6A and 6B, these advantages are provided while at the same time allowing for the same volume within the chamber for insertion of an object or target to be treated. That is, the same size object could be treated within the optical integrating systems of FIGS. 6A/6B and FIGS. 7C/7D. In some embodiments, the distance from the diffuse transmissive baffle 35 and the target 14 is selected to ensure that less than 50%, and preferably less than 25%, and in some cases less than 20%, and in further cases, less than 15% of the light, exiting the surface of diffuse transmissive baffle 35 and facing the treatable target 14, is initially incident on the treatable target 14 in order to allow sufficient light, exiting the diffuse transmissive baffle 35, to impinge directly on the diffusely reflecting surfaces 13 of the chamber and provide generally uniform illumination of the entire treatable target 14. As such, in some embodiments, the distance from the diffuse transmissive baffle 35 and the target 14 is selected to ensure that more than 50%, and preferably more than 75%, and in some cases more than 80%, and in further cases, more than 85% of the light, exiting the surface of diffuse transmissive baffle 35 and facing the treatable target 14, is initially incident on the diffusely reflecting surfaces 13 of the chamber 12 to provide substantially uniform illumination of the treatable target 14.

Figure 7D:
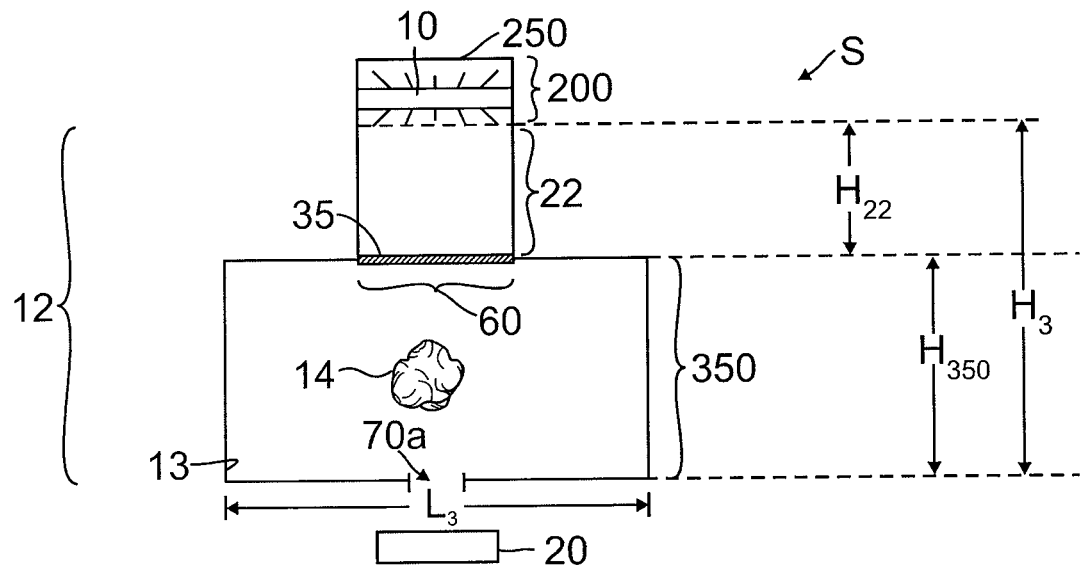
FIG. 7D is a cross-sectional view schematic diagram of the embodiment of the integrating optical system of FIG. 7C taken along a centerline of FIG. 7C.

Referring to FIG. 7D, this cross-sectional view schematic diagram illustrates an integrating optical system S, as shown in FIG. 7C and taken along the centerline $C_3$-$C_3$, comprising a chamber 12, the chamber 12 comprising a main chamber 350 and an auxiliary chamber 22, the main chamber 350 having an input port 60, a bottom output port 70a, and a diffusely reflecting interior surface 13, the auxiliary chamber 22 being coupled with the main chamber 350, a lamp assembly 200 being coupled with the auxiliary chamber 22, a light source 10 disposed outside the chamber 12 but inside the lamp assembly 200, a diffuse transmissive baffle 35 disposed at the input port 60 and in an optical path between the light source 10 and the bottom output port 70a, a detector 20 disposed outside the chamber 12 and at the bottom output port 70a, and a detector 20 (not shown) disposed outside the chamber 12 and at the side output port 70b, wherein the diffuse transmissive baffle 35 comprises a width that is less than that of the main chamber 350, wherein light originates from the light source 10, enters the auxiliary chamber 22, impinges on the diffuse transmissive baffle 35, is diffusely transmitted, impinges on the diffusely reflecting interior surface 13 of the main chamber 350, wherein light is diffusely reflected from the diffusely reflecting interior surface 13 of the main chamber 350, wherein not all light is reflected back toward the light source 10, whereby a diffusely reflected light is provided, and wherein the diffusely reflected light impinges on the detector 20 and may be then measurable by the detector 20, in accordance with an embodiment of the present invention. The lamp assembly 200 comprises a light reflector 250 for enhancing reflection of light from the light source 10 toward the auxiliary chamber 22. The light source 10 comprises a lighting element, such as at least one of a discharge lamp, a microwave-excited arc lamp, an electrodeless arc lamp, a low pressure arc lamp, a medium pressure arc lamp, a high pressure arc lamp, an incandescent lamp, a light emitting diode, and a laser. For example, in this embodiment, the main chamber 350 comprises a height $H_{350}$ of approximately 8 inches, a length $L_3$ of approximately 12 inches, and a width $W_3$ of approximately 12 inches, wherein the diffuse transmissive baffle 35 is disposed at a distance $D_3$ of approximately 0 inches from the input port 60. The auxiliary chamber height $H_{22}$ is as shown in the figure. The total height of the chamber 12 can be expressed as $H_3 = H_{350} + H_{22}$. In particular, this embodiment allows for greater irradiance, e.g., an increase in irradiance of approximately 18%, while maintaining uniformity, and providing a treatment volume with smaller sizes, e.g., a main chamber 350 having a decrease in surface area of approximately 22% for treating a treatable target 14 having the same or comparable volume, than by using the diffuse reflective baffle 30. The decreased main chamber height $H_{350}$ results in a main chamber volume reduction of approximately 33%.

Figure 8A:
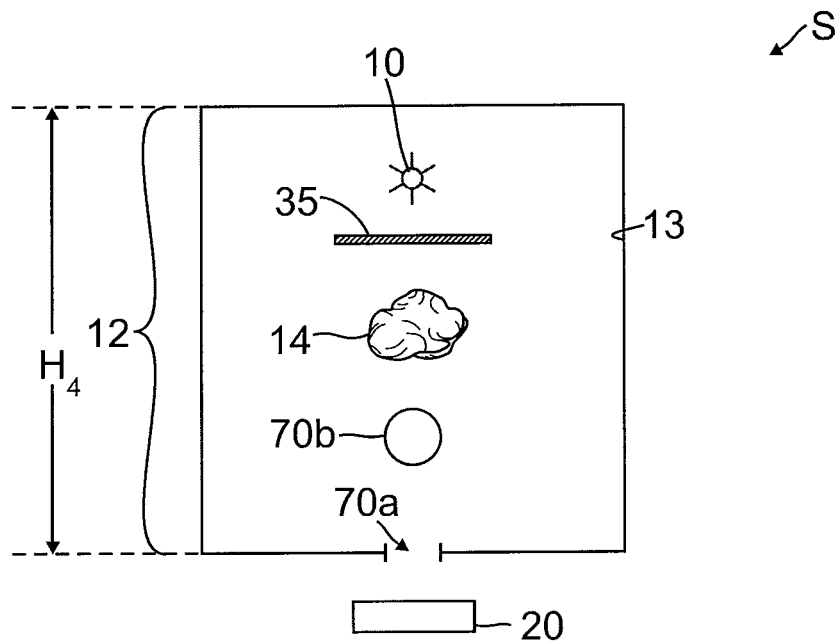
FIG. 8A is an interior view schematic diagram of an integrating optical system, wherein the light source is disposed inside the chamber, in accordance with yet a further embodiment of the present invention.

Referring next to FIG. 8A, while the embodiment of FIG. 4A illustrates an integrating optical system S, wherein the light source 10 as being disposed outside the chamber 12, the light source 10 may alternatively be disposed inside the chamber 12 (FIG. 8A), in accordance with yet a further embodiment of the present invention. The chamber 12 may further comprise a bottom output port 70a and a side output port 70b (not shown). In such a case, the light source 10 is disposed such that the diffuse transmissive baffle 35 is disposed in an optical path between the light source 10 and the treatable target 14. The input port 60 (not shown) may or may not be implemented in this instance. Further, the input port 60 (not shown) may be used for cooling purposes of the light source 10, e.g., for allowing air that has been heated by the light source 10 to escape via natural convection or a forced flow. A lamp assembly 200 is not used in this embodiment.

Figure 8B:
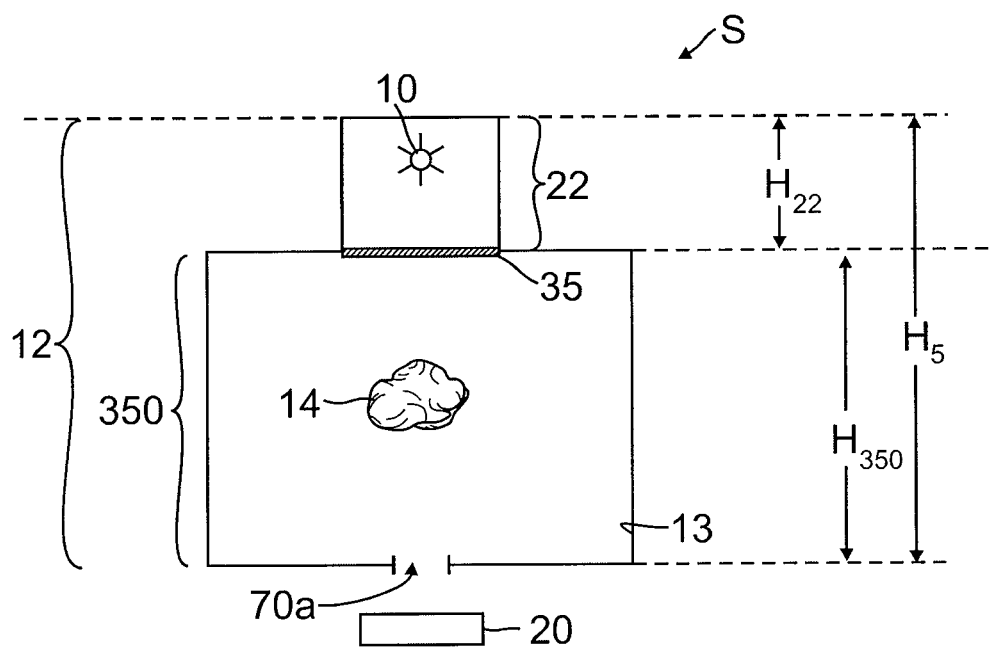
FIG. 8B is an interior view schematic diagram of an integrating optical system, wherein the light source is disposed inside an auxiliary chamber of a chamber, in accordance with yet a further embodiment of the present invention.

Referring next to FIG. 8B, while the embodiment of FIG. 4B illustrates an integrating optical system S, wherein the light source 10 as being disposed outside the chamber 12, the light source 10 may alternatively be disposed inside an auxiliary chamber 22 of a chamber 12, the chamber 12 having a height $H_5$, in accordance with yet a further embodiment of the present invention. The total height of the chamber 12 can be expressed as $H_5=H_{350}+H_{22}$. In this case, the light source 10 is disposed such that the diffuse transmissive baffle 35 is disposed in an optical path between the light source 10 and the treatable target 14. The input port 60 (not shown) may or may not be implemented in this instance. Further, the input port 60 (not shown) may be used for cooling purposes of the light source 10, e.g., for allowing air that has been heated by the light source 10 to escape via natural convection or a forced flow. A lamp assembly 200 is not used in this embodiment.

Figure 9A:
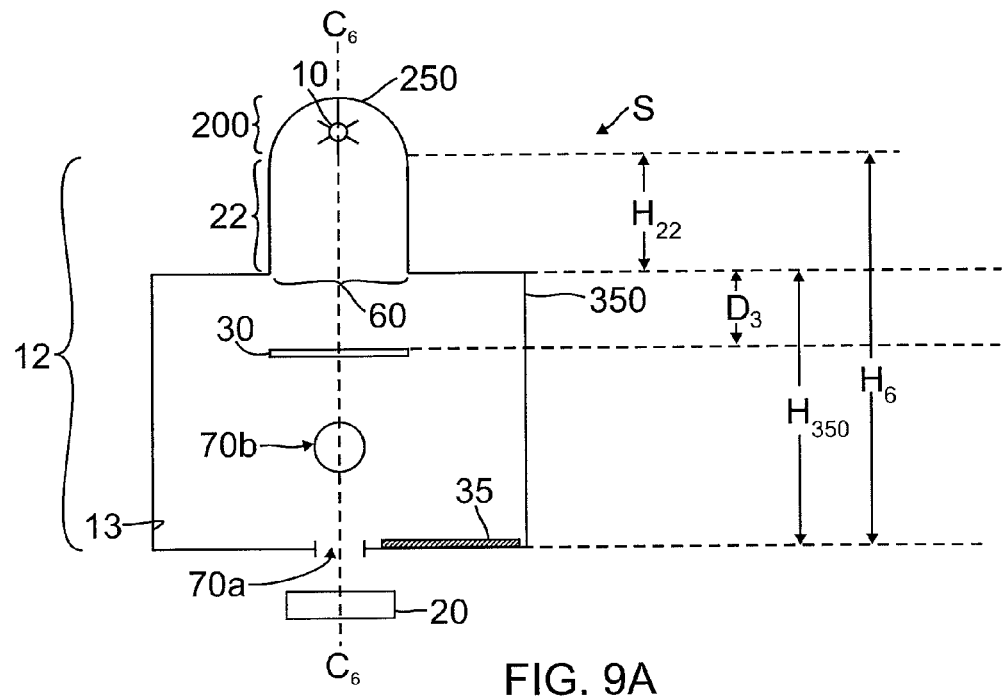
FIG. 9A is an interior view schematic diagram of an integrating optical system, having a centerline and comprising a chamber having a main chamber and an auxiliary chamber, a lamp assembly coupled with the auxiliary chamber, a light source disposed outside the chamber but inside the lamp assembly, a diffuse reflective baffle disposed inside the main chamber between the light source and a bottom output port, a diffuse transmissive baffle disposed in the main chamber and out of the field-of-view of both a detector disposed outside the chamber and at the bottom output port as well as a detector disposed outside the chamber and at a side output port, in accordance with an embodiment.

Referring next to FIG. 9A, this interior view schematic diagram illustrates an integrating optical system S, having a centerline $C_6$-$C_6$ and comprising a chamber 12 having a height $H_6$, the chamber 12 comprising a main chamber 350 and an auxiliary chamber 22, the main chamber 350 having an input port 60, a bottom output port 70a and a side output port 70b, and a diffusely reflecting interior surface 13, the auxiliary chamber 22 being coupled with the main chamber 350, a lamp assembly 200 being coupled with the auxiliary chamber 22, a light source 10 disposed outside the chamber 12 but inside the lamp assembly 200, a diffuse reflective baffle 30 disposed inside the main chamber 350 between the light source 10 and the bottom output port 70a, a diffuse transmissive baffle 35 disposed in the main chamber 350 and out of the field-of-view of detector 20, a detector 20 disposed outside the chamber 12 and at the bottom output port 70a, and a detector 20 (not shown) disposed outside the chamber 12 and at the side output port 70b, wherein the diffuse reflective baffle 30 comprises a width that is less than that of the main chamber 350, wherein light originates from the light source 10, enters the auxiliary chamber 22, impinges on the diffuse reflective baffle 30 and the diffusely reflecting interior surface 13, is diffusely reflected, and impinges on the diffusely reflecting interior surface 13 of the main chamber 350, wherein light is diffusely reflected from the diffusely reflecting interior surface 13 of the main chamber 350, whereby a diffusely reflected light is provided, and wherein the diffusely reflected light impinges on the detector 20 and may be then measurable by the detector 20, in accordance with an embodiment. The lamp assembly 200 comprises a light reflector 250 for enhancing reflection of light from the light source 10 toward the auxiliary chamber 22. The light source 10 comprises a lighting element, such as one or more of a discharge lamp, a microwave-excited arc lamp, an electrodeless arc lamp, a low pressure arc lamp, a medium pressure arc lamp, a high pressure arc lamp, an incandescent lamp, a light emitting diode, and a laser. The total height of the chamber 12 can be expressed as $H_6=H_{350}+H_{22}$. Experimentally, the bottom output port 70a has an exitance of approximately 0.24 W/cm$^2$ while the side output port 70b has an exitance of approximately 0.23 W/cm$^2$ by using this embodiment. This result demonstrates that use of a diffuse transmissive baffle 35 does not significantly contribute to losses of the integrating optical system S, because the irradiance or exitance values are within 5% of those in the embodiments shown in FIGS. 6A, 6B, 7A, and 7B, even though additional diffuse transmissive material is present in the main chamber 350.

Figure 9B:
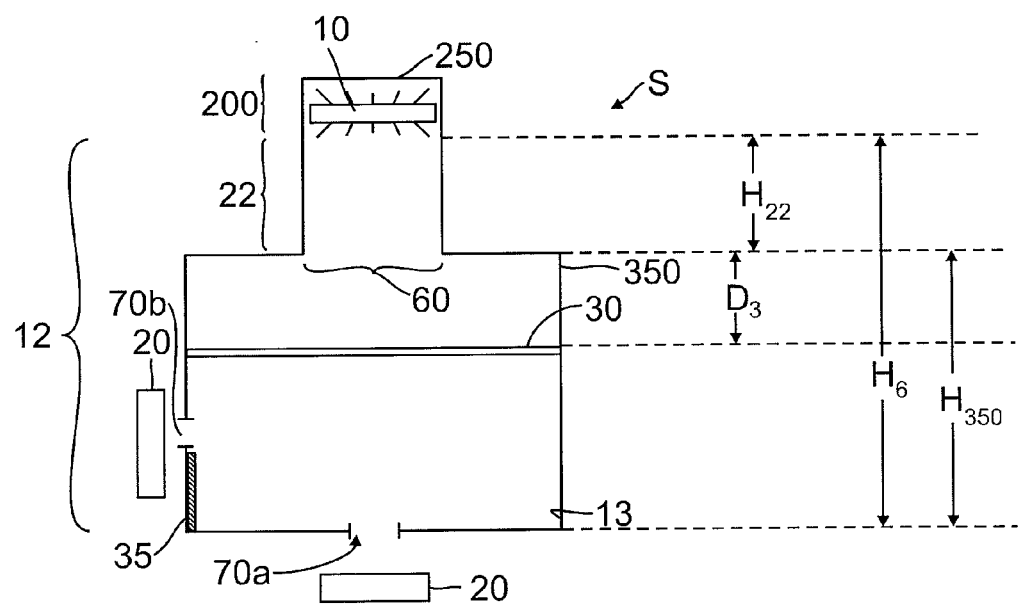
FIG. 9B is a cross-sectional view schematic diagram of the integrating optical system, taken along a centerline, in accordance with the embodiment of FIG. 9A.

Referring next to FIG. 9B, this cross-sectional view schematic diagram illustrates an integrating optical system S, taken at the centerline $C_6$-$C_6$, comprising a chamber 12 having a height $H_6$, the chamber 12 comprising a main chamber 350 and an auxiliary chamber 22, the main chamber 350 having an input port 60, a bottom output port 70a and a side output port 70b, and a diffusely reflecting interior surface 13, the auxiliary chamber 22 being coupled with the main chamber 350, a lamp assembly 200 being coupled with the auxiliary chamber 22, a light source 10 disposed inside the lamp assembly 200, a diffuse reflective baffle 30 disposed inside the main chamber 350 between the light source 10 and the bottom output port 70a, a diffuse transmissive baffle 35 disposed in the main chamber 350 and out of the field-of-view, a detector 20 disposed outside the chamber 12 and at the bottom output port 70a, and a detector 20 disposed outside the chamber 12 and at the side output port 70b, wherein the diffuse reflective baffle 30 comprises a width that is less than that of the main chamber 350, wherein light originates from the light source 10, enters the auxiliary chamber 22, impinges on the diffuse reflective baffle 30 and the diffusely reflecting interior surface 13, is diffusely reflected, and impinges on the diffusely reflecting interior surface 13 of the main chamber 350, wherein light is diffusely reflected from the diffusely reflecting interior surface 13 of the main chamber 350, whereby a diffusely reflected light is provided, and wherein the diffusely reflected light impinges on the detector 20 and may be then measurable by the detector 20, in accordance with the embodiment of FIG. 9A. The lamp assembly 200 comprises a lamp or light reflector 250 for enhancing reflection of light from the light source 10 toward the auxiliary chamber 22, wherein the light reflector 250 comprises a rectangular configuration. The light source 10 comprises a lighting element, such as a discharge lamp, a microwave-excited arc lamp, an electrodeless arc lamp, a low pressure arc lamp, a medium pressure arc lamp, a high pressure arc lamp, an incandescent lamp, a light emitting diode, and a laser. The total height $H_6$ of chamber 12, e.g., of approximately 16.8 inches, is set relative to a distance between the light source 10 and the detector 20. By example only, the diffuse reflective baffle 30 is disposed at a distance of approximately 4 inches from the input port 60 in this embodiment. The total height of the chamber 12 can be expressed as $H_6=H_{350}+H_{22}$. Experimentally, the bottom output port 70a has an exitance of approximately 0.24 W/cm$^2$ while the side output port 70b has an exitance of approximately 0.23 W/cm$^2$ by using this embodiment. This result demonstrates that use of a diffuse transmissive baffle 35 does not significantly contribute to any excessive losses to the integrating optical system S, because the irradiance or exitance or throughput values are within 5% of those in the embodiments shown in FIGS. 6A, 6B, 7A, and 7B, whether it be via absorption.

Figure 10:
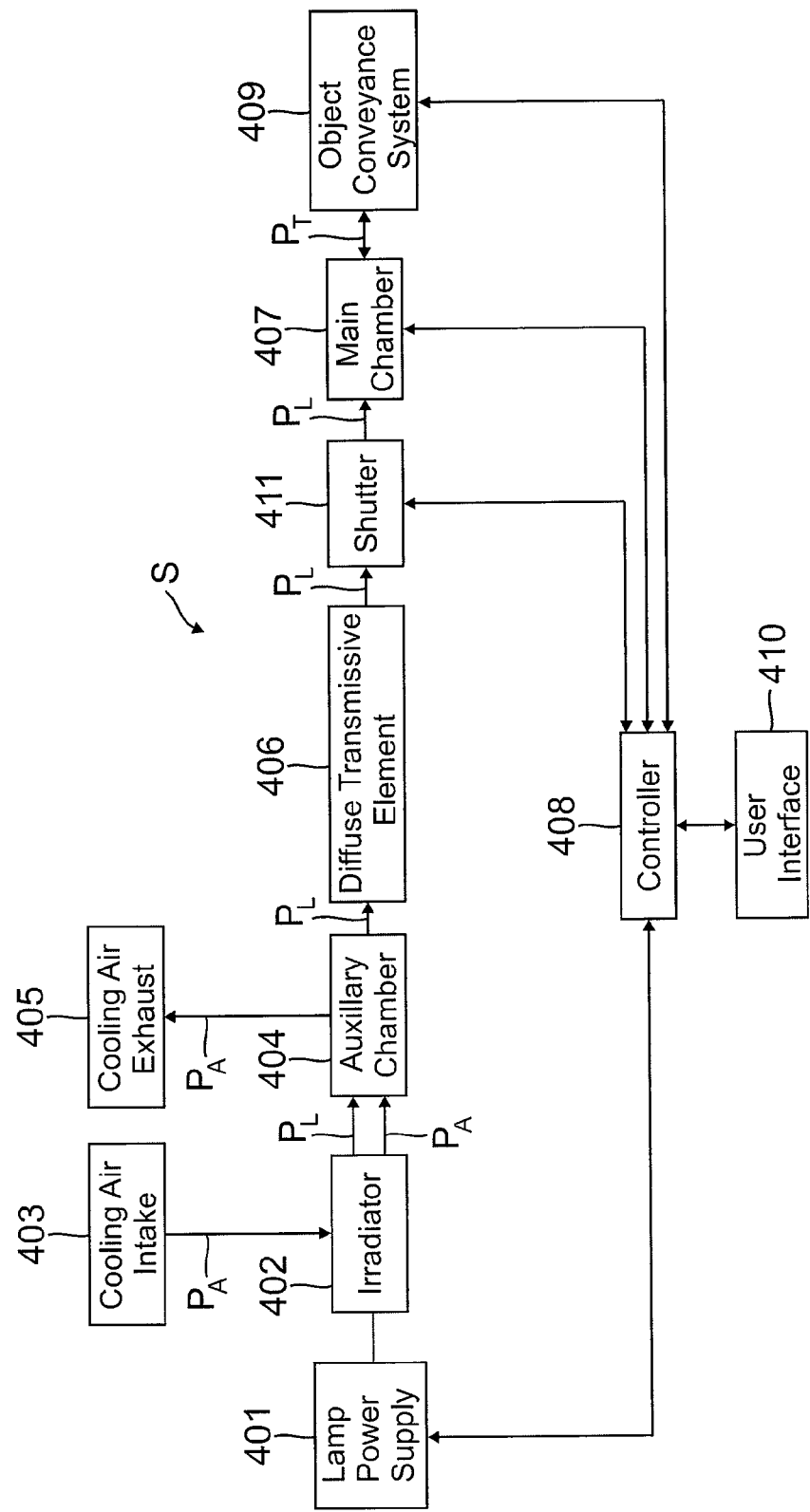
FIG. 10 is a block diagram of some fundamental elements of an integrating optical system, in accordance with an embodiment of the present invention.

Referring next to FIG. 10, this block diagram illustrates some fundamental elements of an integrating optical system S, by example only, in accordance with an embodiment of the present invention. For manual operation, by example only, the system S comprises a lamp power supply 401, an irradiator 402 electronically coupled with, and powered by, the lamp power supply 401, a cooling-air intake 403 and blower (not shown) mechanically coupled with the irradiator 402, an auxiliary chamber 404 mechanically coupled with the irradiator 402, a cooling-air exhaust 405 mechanically coupled with the auxiliary chamber 404, a diffuse transmissive element 406, e.g., comprising a transmissive diffuser, such as a diffuse transmissive baffle 35 (FIGS. 7A and 7B), mechanically coupled with the auxiliary chamber 404 and a main chamber 407 mechanically coupled with, or housing the diffuse transmissive element 406. For automated operation, the system S further comprises controller 408, a shutter 411 electronically or pneumatically coupled with the controller 408 as well as mechanically coupled between the diffuse transmissive element 406 and the main chamber 407, an object or a treatable target conveyance system 409 electronically coupled with the controller 408 and mechanically coupled with the main chamber 407, and a user interface 410 electronically coupled with the controller 408, wherein the lamp power supply 401 and the main chamber 407 are also electronically coupled with the controller 408. The pathway $P_L$ taken by the light is shown as originating at the irradiator 402, into the auxiliary chamber 404, through the diffuse transmissive element 406, though the shutter 411 (if system S is automated), and finally into the main chamber 407. The pathway $P_T$ taken by the treatable target is shown as originating from the object or treatable target conveyance system 409 and then into the main chamber 407, or into proximity of an output port of the main chamber 407, if system S is automated. The pathway $P_A$ taken by the air flow is shown as originating from the cooling-air blower (not shown) from the external atmosphere, through the irradiator 402, into the auxiliary chamber 404, and finally through the cooling-air exhaust 405, and then into the external atmosphere (not shown). The blower is not automatically controlled, but is actuated using an on/off switch. The particular orientation of one element relative to the other may vary, for example, the diffuse transmissive element 406 may be located between the irradiator 402 and the auxiliary chamber 404. Further, the main chamber 407 may be exhausted with air as well. The main chamber 407 may be filled with nitrogen as an inert gas for purging oxygen, thereby providing an inert atmosphere that facilitates the curing process of the treatable target 14 (not shown). Light from the irradiator 402 may be directly coupled to the auxiliary chamber 404, or it may be coupled by a structure or coupling device 80 (FIG. 18), such as one or more of a light guides (not shown) and a lens (not shown).

Figure 11:
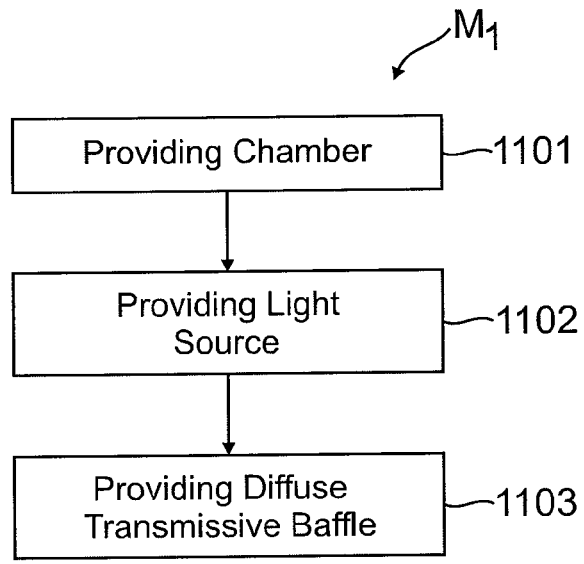
FIG. 11 is flow diagram of a method of fabricating an integrating optical system, in accordance with another embodiment of the present invention.

Referring next to FIG. 11, this flow diagram illustrates a method $M_1$ of fabricating an integrating optical system S, in accordance with an embodiment of the present invention. The method $M_1$ of fabricating an integrating optical system comprises providing at least one chamber, the at least one chamber providing step comprising providing each at least one chamber with at least one aperture and at least one portion comprising a diffuse reflective material, as indicated by block 1101; providing at least one light source, as indicated by block 1102; and providing at least one diffuse transmissive baffle disposed in relation to the at least one chamber in a manner wherein the at least one diffuse transmissive baffle is also disposed in an optical path between the at least one light source and at least one treatable target, wherein the at least one diffuse transmissive baffle is disposed in a manner wherein at least one light-ray originating from the at least one light source is diffusely transmittable from the at least one diffuse transmissive baffle and impingeable on an interior surface of the at least one chamber before being impingeable on the at least one treatable target, as indicated by block 1103. The method $M_1$ may further comprise providing at least one shutter disposed between the at least one light source and the at least one chamber (not shown); and providing at least one lamp assembly, the at least one lamp assembly providing step comprising providing each at least one lamp assembly with at least one light reflector for accommodating the at least one light source, the at least one reflector facilitating reflection of light toward the at least one chamber (not shown).

Figure 12:
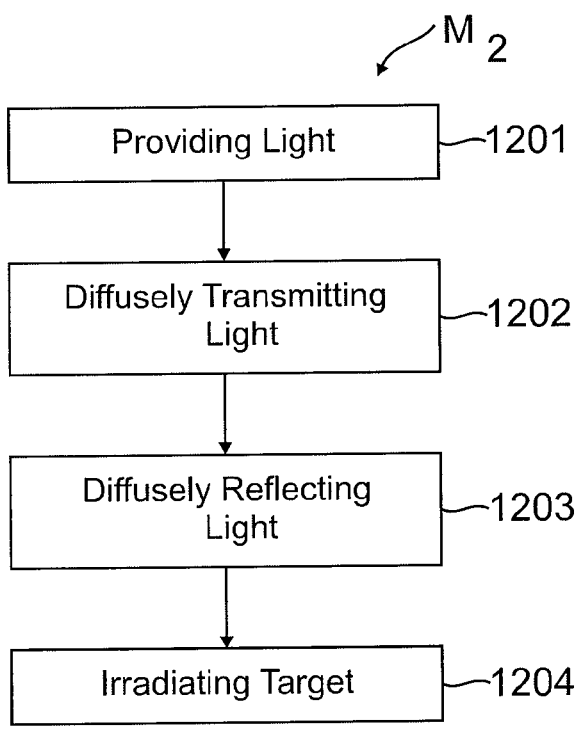
FIG. 12 is a flow diagram of a method of treating a target by way of an integrating optical system, in accordance with yet another embodiment of the present invention.

Referring next to FIG. 12, this flow diagram illustrates a method $M_2$ of treating a target by way of an integrating optical system S, in accordance with an embodiment of the present invention. The method $M_2$ of treating at least one treatable target with light comprises providing light, having at least one light-ray, within a volume from at least one light source, as indicated by block 1201; diffusely transmitting the at least one light-ray being in a direct path to the at least one treatable target by way of at least one diffuse transmissive baffle such that the at least one light-ray impinges on an interior surface of at least one chamber before impinging on the at least one treatable target, as indicated by block 1202; diffusely reflecting the at least one light-ray within the volume for collecting the at least one light, thereby integrating the at least one light-ray, and thereby providing at least one integrated light-ray, as indicated by block 1203; and irradiating the at least one treatable target with the at least one integrated light-ray, thereby providing at least one treated target, as indicated by block 1204.

Figure 13A:
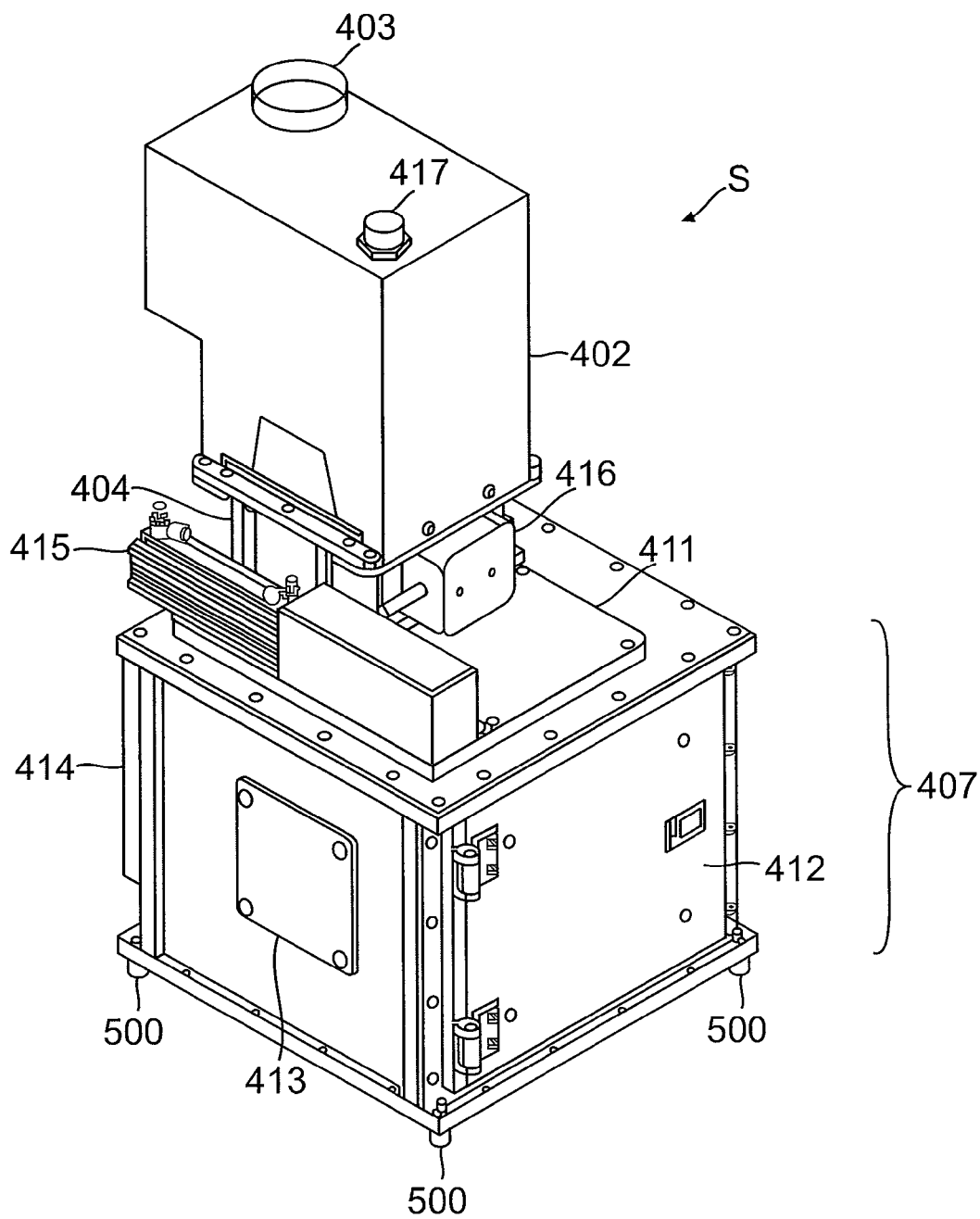
FIG. 13A is a front perspective view diagram of an integrating optical system, in accordance with an embodiment of the present invention.

Referring next to FIG. 13A, this front perspective view diagram illustrates an integrating optical system S, in accordance with an embodiment of the present invention. The system S comprises a lamp power supply 401 (FIG. 10), an irradiator 402 electronically coupled with, and powered by, the lamp power supply 401 (FIG. 10), a cooling-air intake 403 and a blower (not shown) mechanically coupled with the irradiator 402, an auxiliary chamber 404 mechanically coupled with the irradiator 402, a cooling-air exhaust 405 (FIG. 13B) mechanically coupled with the auxiliary chamber 404, a main chamber 407 mechanically coupled with the auxiliary chamber 404, the main chamber for housing a diffuse transmissive element 406 (FIG. 10), such as a diffuse transmissive baffle 35 (FIG. 5A), as well as a treatable target 14 (FIG. 5A), and a junction box 414 mechanically coupled with the main chamber 407. For automated operation, the system S further comprises a controller 408 (FIG. 10) electronically coupled with the junction box 414 (FIGS. 13B and 13C), a shutter 411 with a pneumatic cylinder 415 electronically coupled with the controller 408 (FIG. 10) as well as mechanically coupled between the auxiliary chamber 404 and the main chamber 407, wherein the lamp power supply 401 (FIG. 10) and the main chamber 407 are also electronically coupled with the controller 408 (FIG. 10). The main chamber 407 comprises a door 412 for facilitating placement of the treatable target 14 (FIG. 5A), inter alia. A side access port 413 (FIG. 13B) may be provided on both sides for facilitating, among other things, insertion of a treatable target 14 (FIG. 5A), such as a pipe, a cable, or a catheter, through the main chamber 407 in a continuous fashion, and a plurality of feet 500 for supporting the system S. Alternatively, the pipe or the catheter may comprise a light transmissive material and may act as a target support for flowing through, or otherwise transmitting, a treatable target 14 (FIG. 5A), rather than being the treatable target 14 (FIG. 5A) itself. This alternative embodiment facilitates applications, such as disinfection of fluids, by example only. The irradiator 402 comprises a light source 16 (FIG. 13C), a light reflector 250 (FIG. 13C), and a lamp radio frequency (RF) detector 416. The light source 16 (FIG. 13C) is microwave-excitable. The lamp or light reflector 250 (FIG. 13C) redirects the light-rays into the auxiliary chamber 404. The detector 416 senses any microwave leaks from the light source 16 (FIG. 13C) and initiates a shut-down of the light source 16 (FIG. 13C) in the event of such leak. The irradiator 402 further comprises at least one electrical connector 417 for facilitating connection to the lamp power supply 401 (FIG. 10), inter alia.

Figure 13B:
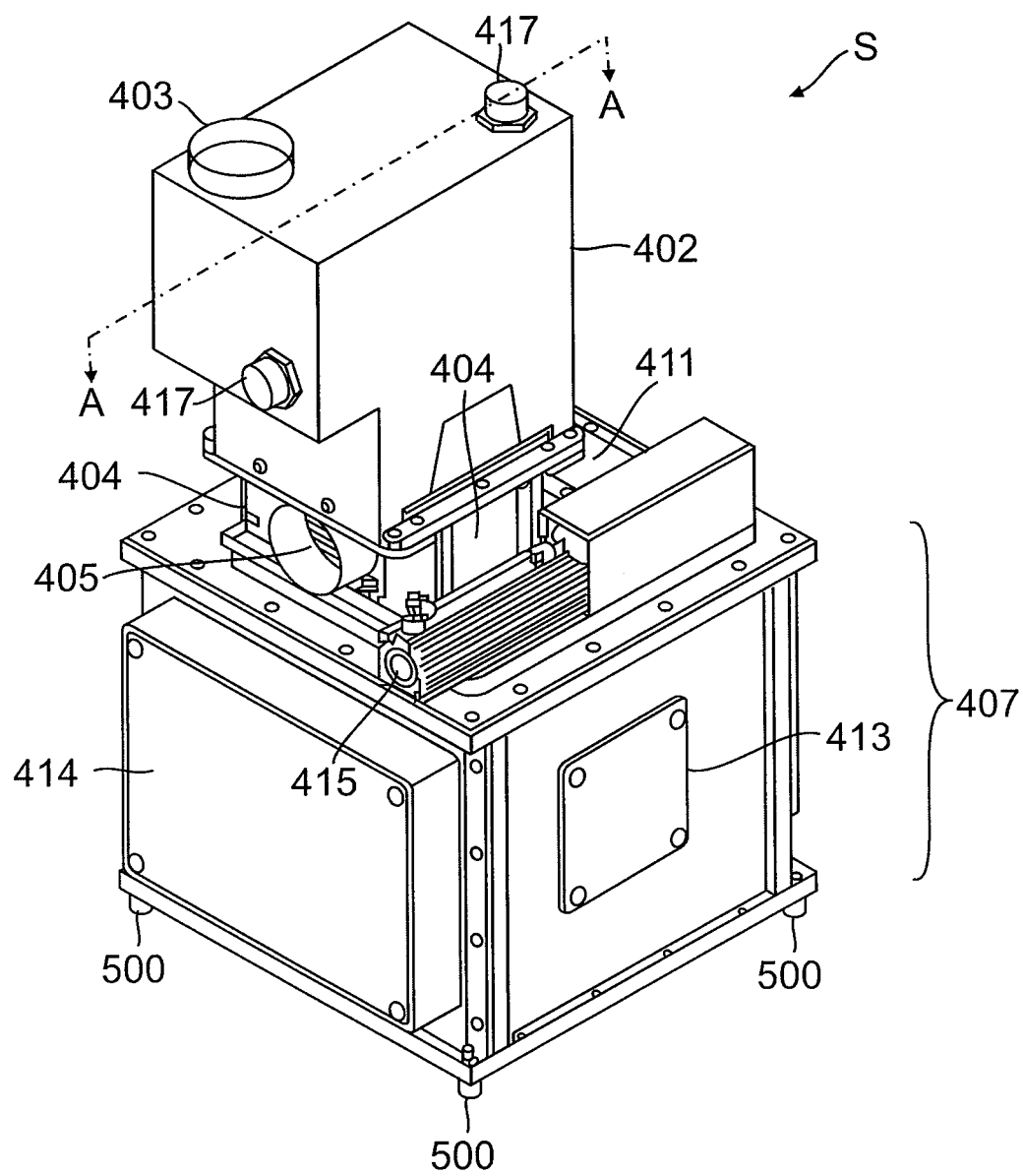
FIG. 13B is a rear perspective view diagram of the embodiment of the integrating optical system of FIG. 13A.

Referring next to FIG. 13B, this rear perspective view diagram illustrates an integrating optical system S, in accordance with an embodiment of the present invention as shown in FIG. 13A. The system S comprises a lamp power supply 401 (FIG. 10), an irradiator 402 electronically coupled with, and powered by, the lamp power supply 401 (FIG. 10), a cooling-air intake 403 and a blower (not shown) mechanically coupled with the irradiator 402, an auxiliary chamber 404 mechanically coupled with the irradiator 402, a cooling-air exhaust 405 mechanically coupled with the auxiliary chamber 404, a main chamber 407 mechanically coupled with the auxiliary chamber 404, the main chamber 407 for housing a diffuse transmissive element 406 (FIG. 10), such as a diffuse transmissive baffle 35 (FIG. 5A), as well as a treatable target 14 (FIG. 5A), and a junction box 414 mechanically coupled with the main chamber 407. For automated operation, the system S further comprises a controller 408 (FIG. 10) electronically coupled with the junction box 414, a shutter 411 with a pneumatic cylinder 415 electronically coupled with the controller 408 (FIG. 10) as well as mechanically coupled between the auxiliary chamber 404 and the main chamber 407, wherein the lamp power supply 401 (FIG. 10) and the main chamber 407 are also electronically coupled with the controller 408 (FIG. 10). The main chamber 407 comprises a door 412 (FIG. 13A) for facilitating placement of the treatable target 14 (FIG. 5A), inter alia, a side access port 413 for facilitating positioning of a diffuse transmissive element 406 (FIG. 10), and a plurality of feet 500 for supporting the system S. The irradiator 402 comprises a light source 16 (FIG. 13C), a light reflector 250 (FIG. 13C), and a lamp radio frequency (RF) detector 416 (FIG. 13A). The light source 16 (FIG. 13C) is microwave-excitable. The diffuse transmissive element 406 (FIG. 10) may comprise a diffuse transmissive baffle 35, as described, supra. The light reflector 250 (FIG. 13C) redirects the light-rays into the auxiliary chamber 404. The detector 416 (FIG. 13A) senses any microwave leaks from the light source 16 (FIG. 13C) and initiates a shut-down of the light source 16 (FIG. 13C) in the event of such leak. The irradiator 402 further comprises at least one electrical connector 417 for facilitating connection to the lamp power supply 401 (FIG. 10), inter alia. A cross-section A-A is taken to show the interior of the system S, as described, infra, in relation to FIG. 13C.

Figure 13C:
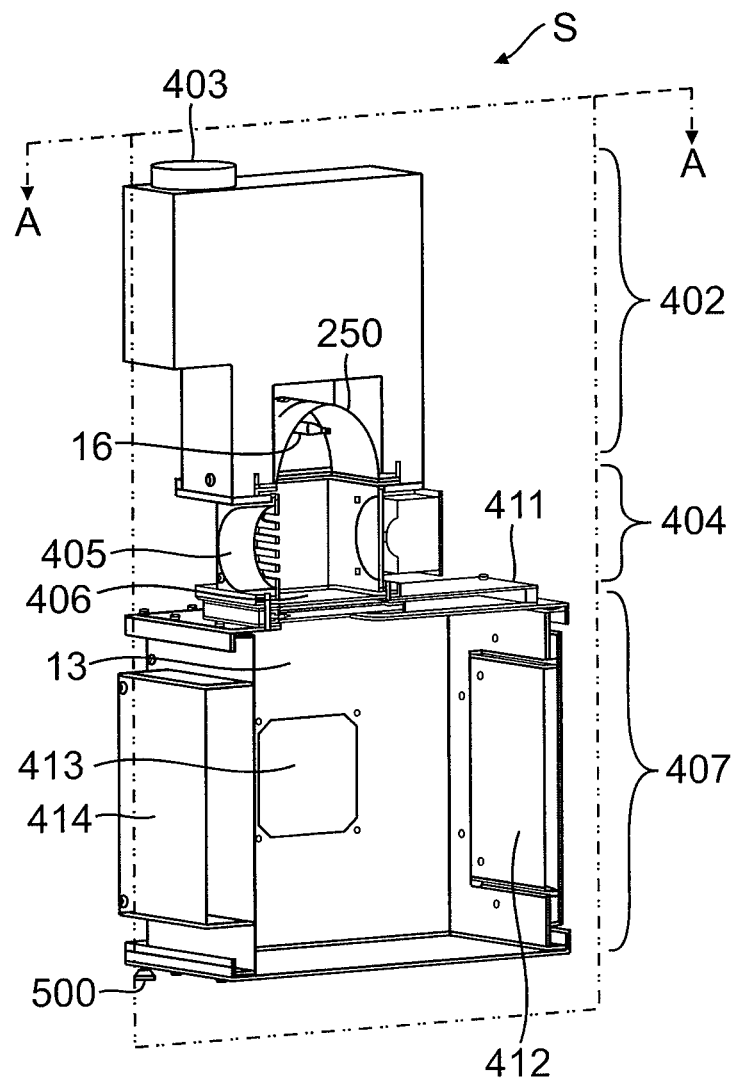
FIG. 13C is a perspective interior cut-away view diagram of the embodiment of the integrating optical system of FIG. 13A.

Referring next to FIG. 13C, this cross-sectional perspective view diagram illustrates an integrating optical system S taken at the cross-section A-A, in accordance with an embodiment of the present invention as shown in FIG. 13B. The system S comprises a lamp power supply 401 (FIG. 10), an irradiator 402 electronically coupled with, and powered by, the lamp power supply 401 (FIG. 10), a cooling-air intake 403 and a blower (not shown) mechanically coupled with the irradiator 402, an auxiliary chamber 404 mechanically coupled with the irradiator 402, a cooling-air exhaust 405 mechanically coupled with the auxiliary chamber 404, a main chamber 407 mechanically coupled with the auxiliary chamber 404, the main chamber 407 for housing a diffuse transmissive element 406 (FIG. 10), such as a diffuse transmissive baffle 35 (FIG. 5A), as well as a treatable target 14 (FIG. 5A), and a junction box 414 mechanically coupled with the main chamber 407. Other methods of support are presented. For automated operation, the system S further comprises a controller 408 (FIG. 10) electronically coupled with the junction box 414, a shutter 411 with a pneumatic cylinder 415 (FIG. 13B) electronically coupled with the controller 408 (FIG. 10) as well as mechanically coupled between the auxiliary chamber 404 and the main chamber 407, wherein the lamp power supply 401 (FIG. 10) and the main chamber 407 are also electronically coupled with the controller 408 (FIG. 10). The diffuse transmissive element 406 may be supported by sandwiching it between the auxiliary chamber 404 and the shutter 411, or more generally by sandwiching it between two of the elements, as described in relation to FIG. 10, such that the diffuse transmissive element 406 lies in the optical path between the irradiator 402 and the treatable target 14 (FIG. 5A). The main chamber 407 comprises a door 412 (FIG. 13A) for facilitating placement of the treatable target 14 (FIG. 5A), inter alia, a side access port 413 for facilitating positioning of a diffuse transmissive element 406, and a plurality of feet 500 for supporting the system S. The irradiator 402 comprises a light source 16, a light reflector 250, and a lamp radio frequency (RF) detector 416 (FIG. 13A). The light source 16 is microwave-excitable. The light reflector 250 redirects the light-rays into the auxiliary chamber 404. The detector 416 (FIG. 13A) senses any microwave leaks from the light source 16 and initiates a shut-down of the light source 16 in the event of such leak. The irradiator 402 further comprises at least one electrical connector 417 (FIG. 13B) for facilitating connection to the lamp power supply 401 (FIG. 10), inter alia.

Figure 13D:
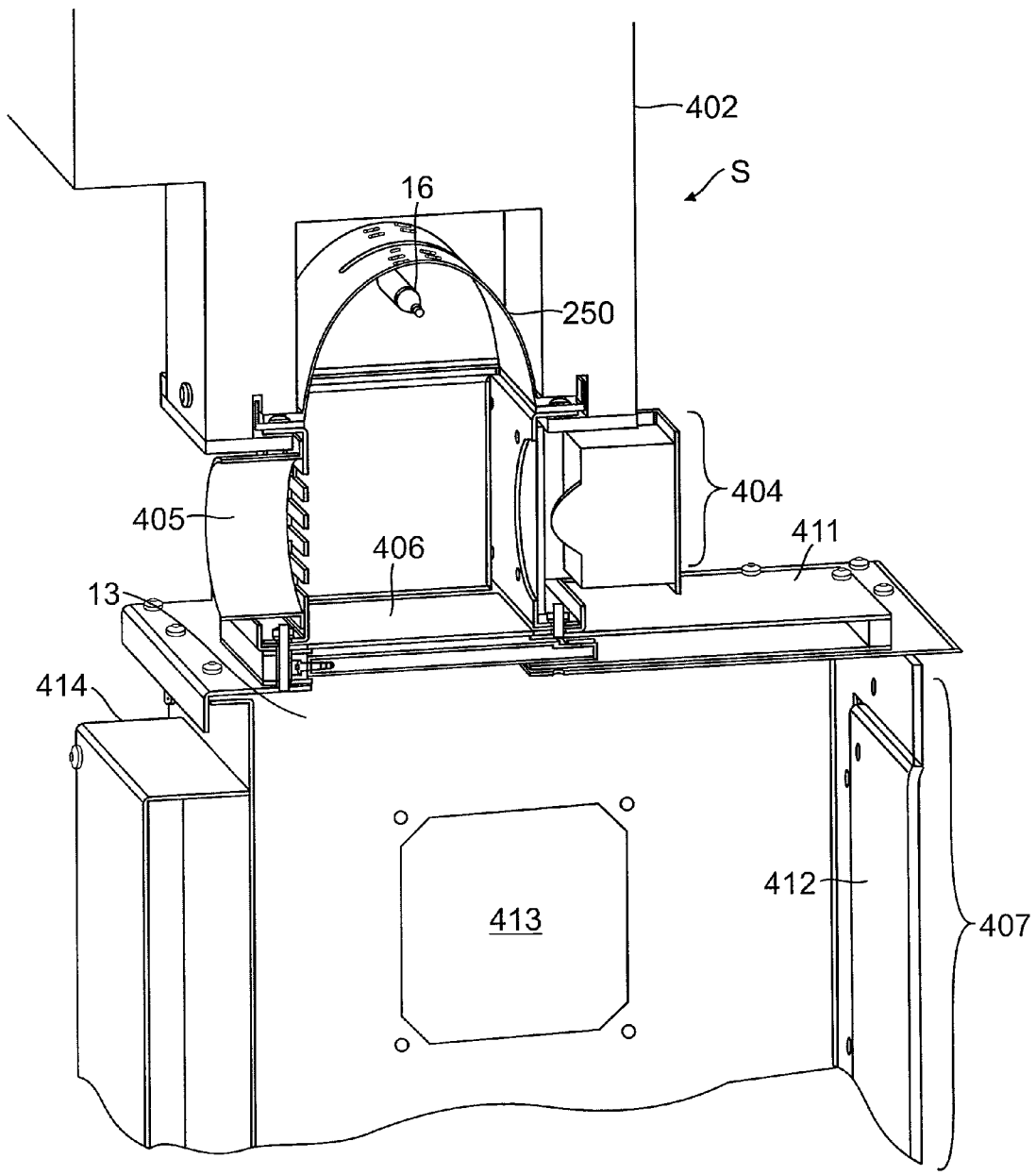
FIG. 13D is a close-up cross-sectional perspective view diagram of the embodiment of the integrating optical system of FIG. 13C.

Referring next to FIG. 13D, this close-up cross-sectional perspective view diagram illustrates an integrating optical system S taken at the cross-section A-A, in accordance with an embodiment of the present invention as shown in FIG. 13C. The main chamber 407 houses a diffuse transmissive element 406 (FIG. 10), such as a diffuse transmissive baffle 35 (FIG. 5A). For automated operation, the system S further comprises a controller 408 (FIG. 10) electronically coupled with the junction box 414, a shutter 411 with a pneumatic cylinder 415 (FIG. 13B) electronically coupled with the controller 408 (FIG. 10) as well as mechanically coupled between the auxiliary chamber 404 and the main chamber 407, wherein the lamp power supply 401 and the main chamber 407 are also electronically coupled with the controller 408. The diffuse transmissive element 406 may be supported by sandwiching it between the auxiliary chamber 404 and the shutter 411, or more generally by sandwiching it between two of the elements, as described in relation to FIG. 10, such that the diffuse transmissive element 406 lies in the optical path between the irradiator 402 and the treatable target 14 (FIG. 5A). Locating the diffuse transmissive baffle 406 at the interface between the auxiliary chamber 404 and the main chamber 407 prevents the cooling air, exhausting the irradiator 402 through the reflector 250, from entering the main chamber 407, and causes the cooling-air to exit through the cooling-air exhaust 405. The irradiator 402 comprises a light source 16, a light reflector 250, and a lamp radio frequency (RF) detector 416 (FIG. 13A). The light source 16 is microwave-excitable. The light reflector 250 redirects the light-rays into the auxiliary chamber 404.

In some embodiments of the present invention, the diffuse transmissive baffle 35 facilitates passage of light from the light source 10 through the aperture or input port 60 of the chamber 12 and onto the treatable target 14 and may comprise a material, such as a high-temperature-resistant material, an aluminum oxide, a polycrystalline aluminum oxide, a polycrystalline sapphire, an optical filter, a quartz, an opaled quartz, a fritted quartz, a sandblasted quartz, a bead-blasted quartz, a sapphire, a sandblasted sapphire, a bead-blasted sapphire, an acid-etched quartz, an acid-etched sapphire, a ground quartz, and a ground sapphire. Acid etching may be performed using a strong acid, such as hydrofluoric acid (HF) for improving the uniformity of irradiance on a treatable target disposed either inside or outside a chamber. Thus, the diffusing surface may be formed by a technique, such as etching, chemical etching, acid etching, sandblasting, bead-blasting, grinding, and opaling. The diffuse transmissive element 406 may comprise at least one diffuse transmissive surface, e.g., one or both sides. The diffuse transmissive element 406 is configurable to selectively reflect or absorb light in certain ranges of wavelength, thereby filtering such light from the chamber 12.

Figure 14A:
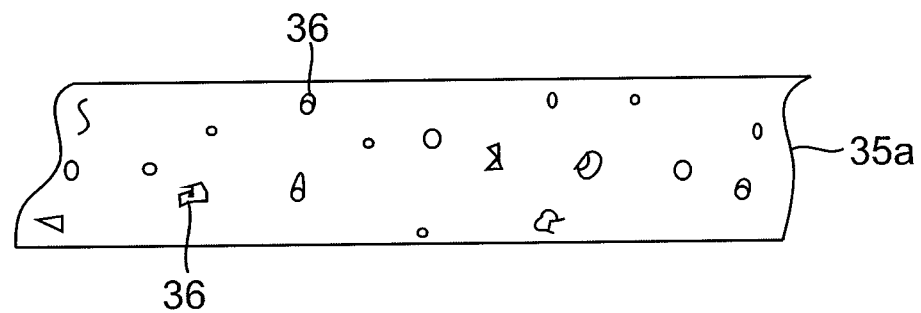
FIG. 14A is a side cut-away view diagram of a diffuse transmissive element, comprising a volume diffusing material, such as a material having scattering or diffusing sites, in accordance with a further embodiment of the present invention.

Referring next to FIG. 14A, this side cut-away view diagram illustrates a diffuse transmissive element 35a, comprising a volume diffusing material, such as a material having scattering or diffusing sites 36, e.g., a pot opal, a fitted quartz, a quartz having a distribution of voids, a quartz having a distribution of scattering sites, a quartz having a distribution of impurities, a quartz having a distribution of dopants, in accordance with a further embodiment of the present invention. The fritted quartz may contain scattering features on the order of nanometers or microns. The volume diffusing material may also comprise a plurality of diffusing surface elements laminated into a single structure.

Figure 14B:
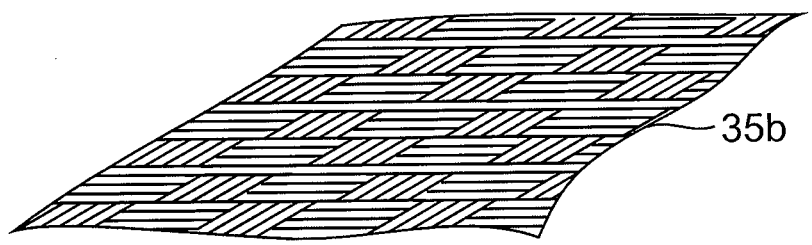
FIG. 14B is a perspective cut-away view diagram of a diffuse transmissive element, comprising a volume diffusing material, such as a quartz felt, in accordance with a further embodiment of the present invention.

Referring next to FIG. 14B, this perspective cut-away view diagram illustrates a diffuse transmissive element 35b, comprising a volume diffusing material, such as one or more of a quartz felt and a quartz wool, in accordance with a further embodiment of the present invention.

Figure 14C:
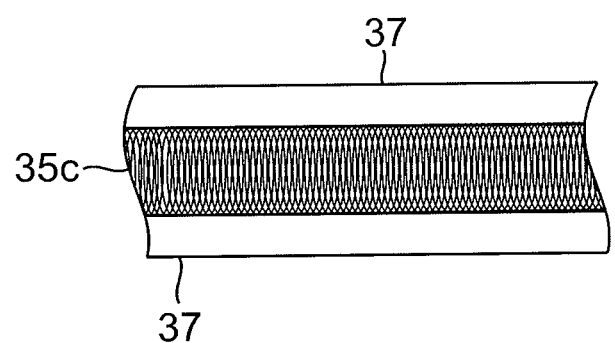
FIG. 14C is a side cut-away view diagram of a diffuse transmissive element, comprising a volume diffusing material, such as a quartz wool or a randomly oriented transmissive fiber sandwiched between optically transparent support members, in accordance with a further embodiment of the present invention.

Referring next to FIG. 14C, this side cut-away view diagram illustrates a diffuse transmissive element 35c, comprising a volume diffusing material, such as one or more of a quartz wool, quartz beads, small quartz pieces, and a randomly oriented transmissive fiber sandwiched between optically transparent support members 37, in accordance with a further embodiment of the present invention.

Figure 15A:
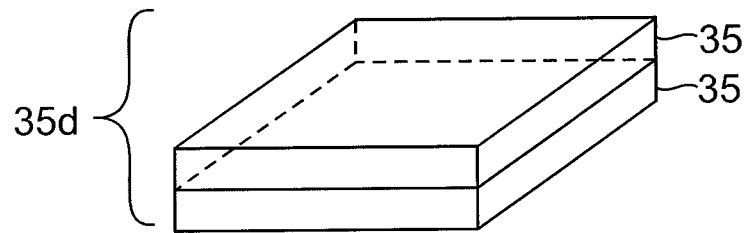
FIG. 15A is a perspective view diagram of a diffuse transmissive element, comprising a plurality of diffuse transmissive baffles, such as two diffuse transmissive baffles being disposed adjacent one another in a stacking relationship, in accordance with a further embodiment of the present invention.

Referring next to FIG. 15A, this perspective view diagram illustrates a diffuse transmissive element 35d, comprising a plurality of diffuse transmissive baffles 35, such as two diffuse transmissive baffles 35 being adjacently disposed in relation to one another, each diffuse transmissive baffles 35 contacting another diffuse transmissive baffle 35 of the plurality of diffuse transmissive baffles 35, e.g., in a stacking relationship by example only, in accordance with a further embodiment of the present invention. Either surface or both surfaces of each diffuse transmissive baffle 35 of the plurality of the diffuse transmissive baffles 35 may be diffuse transmitting.

Figure 15B:
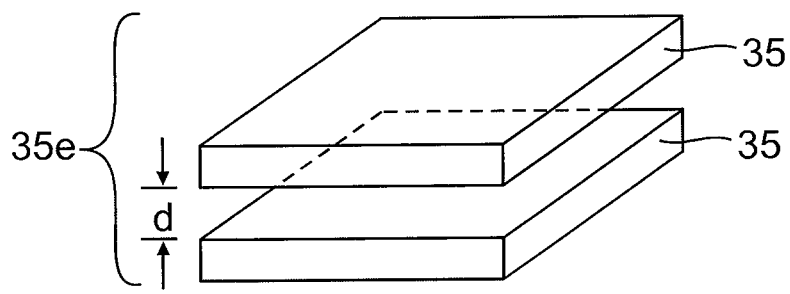
FIG. 15B is a perspective view diagram of a diffuse transmissive element, comprising a plurality of diffuse transmissive baffles, such as two diffuse transmissive baffles being spaced-apart from one another in a stacking relationship, in accordance with a further embodiment of the present invention.

Referring next to FIG. 15B, this perspective view diagram illustrates a diffuse transmissive element 35e, comprising a plurality of diffuse transmissive baffles 35, such as two diffuse transmissive baffles 35 being spaced-apart from one another by a distance d in a range of up to approximately 4 inches, e.g., a spacing being disposed between each diffuse transmissive baffle 35 of the plurality of diffuse transmissive baffles 35 with the plurality of diffuse transmissive baffles 35 being in a stacking relationship, but non-contacting, by example only, in accordance with a further embodiment of the present invention. Likewise either surface or both surfaces of each diffuse transmissive baffle 35 of the plurality of the diffuse transmissive baffles 35 may be diffuse transmitting.

Figure 15C:
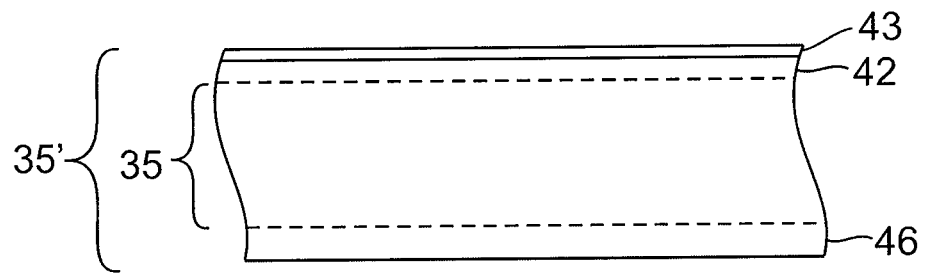
FIG. 15C, is a side cut-away view diagram of a diffuse transmissive baffle, further comprising a polished surface, a non-reflective side, and dichroic material, to form a "hot mirror," in accordance with yet a further embodiment of the present invention.

Referring next to FIG. 15C, this side cut-away view of a diffuse transmissive baffle 35, further comprising a polished surface 42, such as a highly polished surface to form a "hot mirror" 35', by example only, for reflecting the IR component of light, e.g., >approximately 800 nm, thereby preventing the unwanted IR component from entering the chamber 12 (as described, supra), in accordance with yet a further embodiment of the present invention. Further, a coating may be included on the diffuse transmissive baffle 35 that reflects the IR component as well as the visible component, e.g., >approximately 600 nm, for reducing heat being generated on a treatable target 14 (as described, supra) that would otherwise damage the treatable target 14 (as described, supra) or its treated surface. The hot mirror 35' may comprise a polished surface 42 for reflecting a type, or wavelength, of light, such as one or more of infrared light, visible light and ultraviolet light. Further, the polished surface 42 may comprise a dichroic material 43 for facilitating reflecting infrared light and/or visible light. The non-reflective side 46 is treated to form a diffuse transmissive surface providing the advantages, inter alia, described, supra. The hot mirror side of the hot mirror 35' is preferably disposed facing the lamp or the light source 10; however, disposing the diffusive side of a diffuse transmissive baffle 35 will also be serviceable.

Figure 16A:
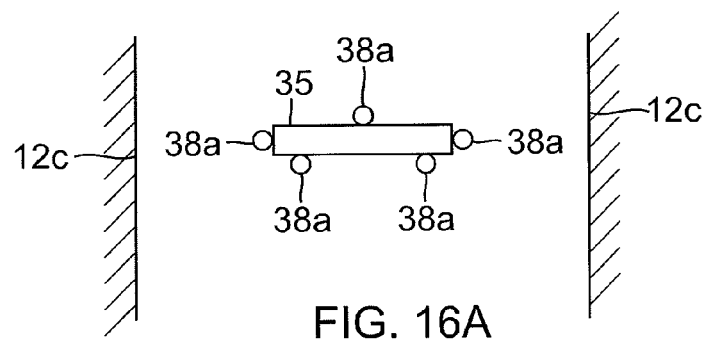
FIG. 16A is a front view schematic diagram of a baffle support structure for retaining a diffuse transmissive baffle, comprising a combination of upper tangs, lower tangs, and side tangs, in accordance with a further embodiment of the present invention.

Referring next to FIG. 16A, this front view schematic diagram illustrates a baffle support structure for retaining a diffuse transmissive baffle 35, by example only, in accordance with a further embodiment of the present invention. The baffle support structure comprises a configuration, such as a combination 38a of upper tangs, lower tangs, and side tangs, e.g., preferably approximately four tangs disposed below, approximately two tangs disposed above, and approximately two tangs disposed alongside the diffuse transmissive baffle 35, mechanically coupled to at least one sidewall 12c of the chamber 12 (as described, supra) and a plurality of fasteners, e.g., preferably approximately four screws disposed below, approximately two screws disposed above, and approximately two screws disposed alongside the diffuse transmissive baffle 35, wherein the diffuse transmissive baffle extends to touch at least two sidewalls 12c. The tangs may comprise a material, such as one or more of an optically transparent material and an optically reflective material.

Figure 16B:
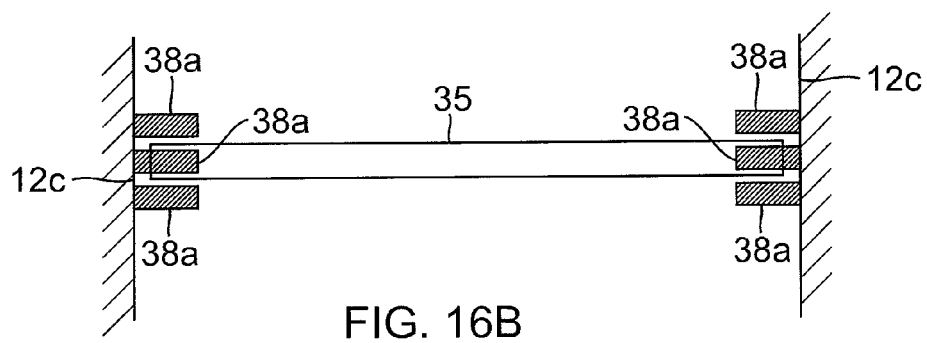
FIG. 16B is a side view schematic diagram of a baffle support structure for supporting a diffuse transmissive baffle, as shown in FIG. 16A, in accordance with a further embodiment of the present invention.

Referring next to FIG. 16B, this side view schematic diagram illustrates a baffle support structure for supporting a diffuse transmissive baffle 35, wherein the baffle support structure may comprise a combination 38a of upper tangs, lower tangs, and side tangs and may be optically transparent, as shown in FIG. 16A, in accordance with a further embodiment of the present invention.

Figure 16C:
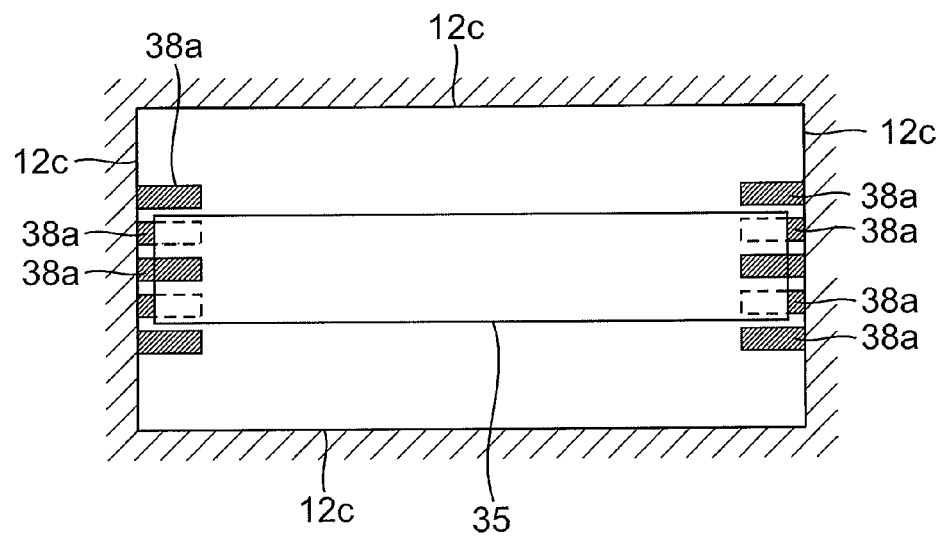
FIG. 16C is a top view schematic diagram of a baffle support structure for supporting a diffuse transmissive baffle, as shown in FIG. 16A, in accordance with a further embodiment of the present invention.

Referring next to FIG. 16C, this top view schematic diagram illustrates a baffle support structure for supporting a diffuse transmissive baffle 35, wherein the baffle support structure may comprise a combination 38a of upper tangs, lower tangs, and side tangs and may be optically transparent, as shown in FIG. 16A, in accordance with a further embodiment of the present invention.

Figure 16D:
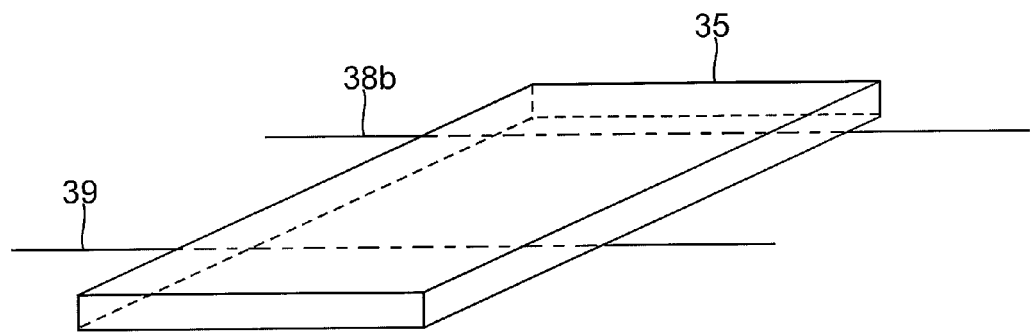
FIG. 16D is a perspective view schematic diagram of a baffle support structure, comprising an array of small diameter wires, in accordance with a further embodiment of the present invention.

Referring next to FIG. 16D, this perspective view schematic diagram illustrates a baffle support structure, comprising an array of small diameter wires 38b for supporting a diffuse transmissive baffle 35, by example only, in accordance with a further embodiment of the present invention. The wires 38b may comprise a material, such as one or more of an optically transparent material and an optically reflective material.

Figure 16E:
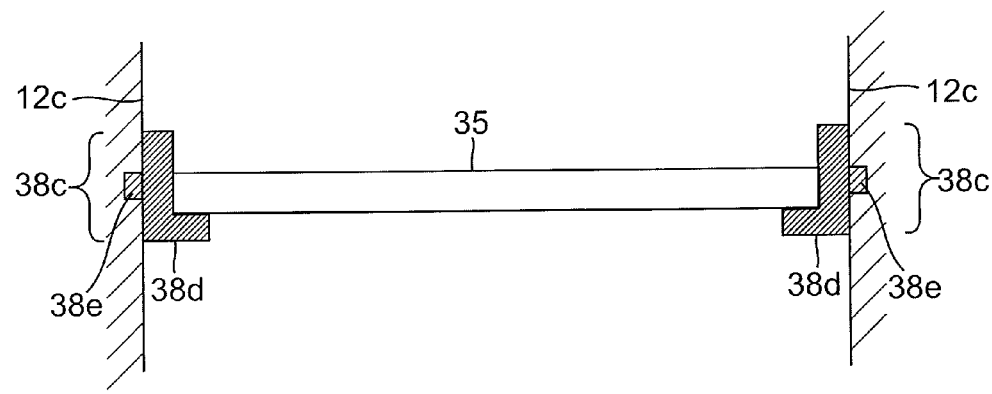
FIG. 16E is a side view schematic diagram of a baffle support structure, comprising a screw and shelf member combination, in accordance with a further embodiment of the present invention.

Referring next to FIG. 16E, this side view schematic diagram illustrates a baffle support structure, comprising a combination 38c of a screw and shelf member, for supporting a diffuse transmissive baffle 35, by example only, in accordance with a further embodiment of the present invention. The shelf member 38d comprises a reflecting material, such as Teflon® and Spectalon®, being fastened to a sidewall 12c of the chamber 12 (as described, supra) via a screw 38e, by example only.

Figure 17A:
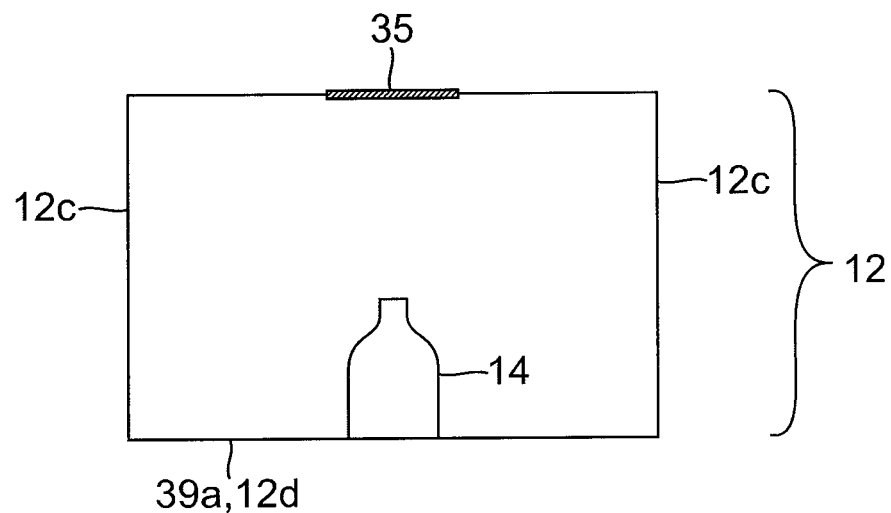
FIG. 17A is an interior side view schematic diagram of a target support structure, comprising a floor of the chamber, in accordance with a further embodiment of the present invention.

Referring next to FIG. 17A, this interior side view schematic diagram illustrates a target support structure, comprising a structure 39a, such as a floor 12d of the chamber 12, for supporting a treatable target 14, by example only, in accordance with a further embodiment of the present invention. Alternatively, the support structure may comprise a conveyance system (not shown), such as a conveyor belt (not shown) moving through the chamber 12 upon which the treatable target 14 may be disposed for moving into and through the chamber 12.

Figure 17B:
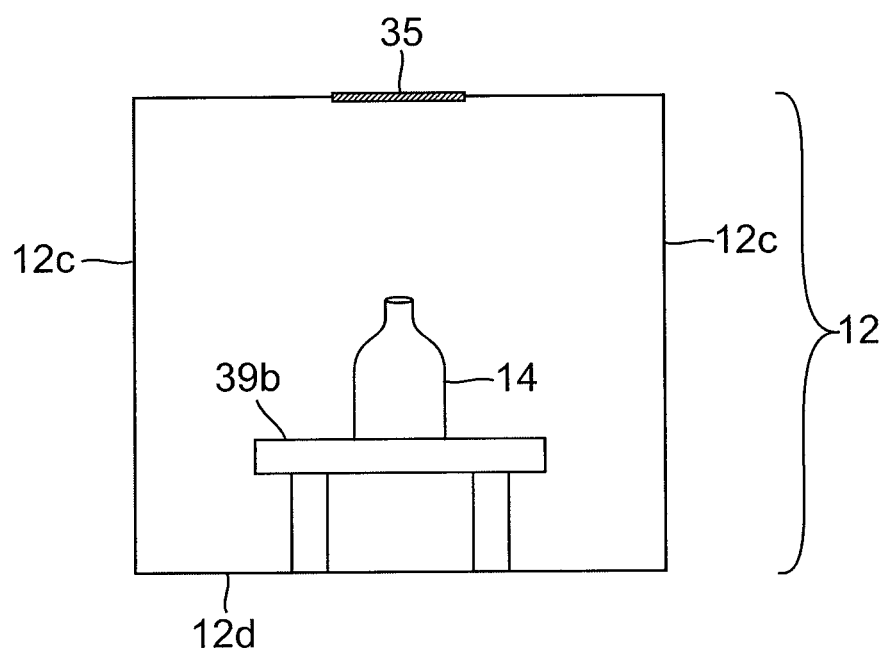
FIG. 17B is an interior side view schematic diagram of a target support structure, comprising a table, in accordance with a further embodiment of the present invention.

Referring next to FIG. 17B, this interior side view schematic diagram illustrates a target support structure, comprising a table 39b or shelf (not shown) disposed on a floor 12d of the chamber 12, for supporting a treatable target 14, by example only, in accordance with a further embodiment of the present invention. The table 39b or shelf (not shown) comprises an optically transparent material, such as quartz. The table 39b or shelf (not shown) may comprise a material, e.g., one or more of an optically transparent material, such as a quartz, and an optically reflective material, such as a fluorinated polymer and Teflon®.

Figure 17C:
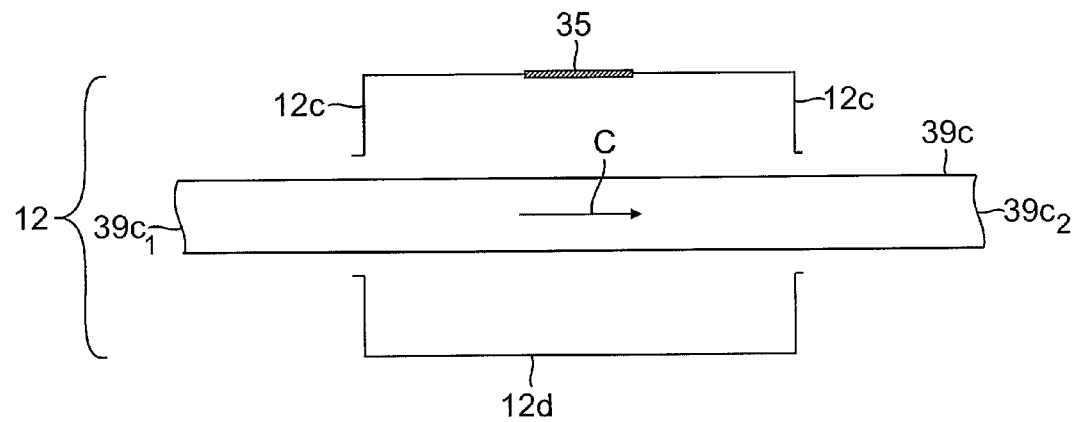
FIG. 17C is an interior side view schematic diagram of a continuous pipe, the pipe being a treatable target itself or alternatively being a target support structure, in accordance with a further embodiment of the present invention.

Referring next to FIG. 17C, this interior side view schematic diagram illustrates a treatable target 14 (as described, supra), comprising a continuous pipe 39c disposed the chamber 12, the chamber 12 having sidewalls 12c and a floor 12d, by example only, in accordance with a further embodiment of the present invention. The continuous pipe 39c is inserted through a first sidewall of the sidewalls 12c and exits thru a second sidewall of the sidewalls 12c, and is fed in a direction C, by example only.

Still referring to FIG. 17C, the continuous pipe 39c may alternatively act as a target support structure, wherein the continuous pipe 39c is disposed through the sidewalls 12c of the chamber 12, as previously described, but can also be used for supporting, feeding, and/or flowing a treatable target 14 (as described, supra), by example only, in accordance with a further embodiment of the present invention. The treatable target 14 (as described, supra) may be inserted through a first end $39c_1$ of the continuous pipe 39c, and may be optionally fed, flowed, or otherwise conveyed through the continuous pipe 39c to a second end $39c_2$ of the continuous pipe 39c in a direction C, by example only. The continuous pipe 39c may be alternatively inserted and removed through only one opening in the sidewall 12c. This embodiment is conducive to use with a treatable target 14 (as described, supra) that comprises a solid, a gel, or a fluid, such as water, oil, or gas.

Figure 17D:
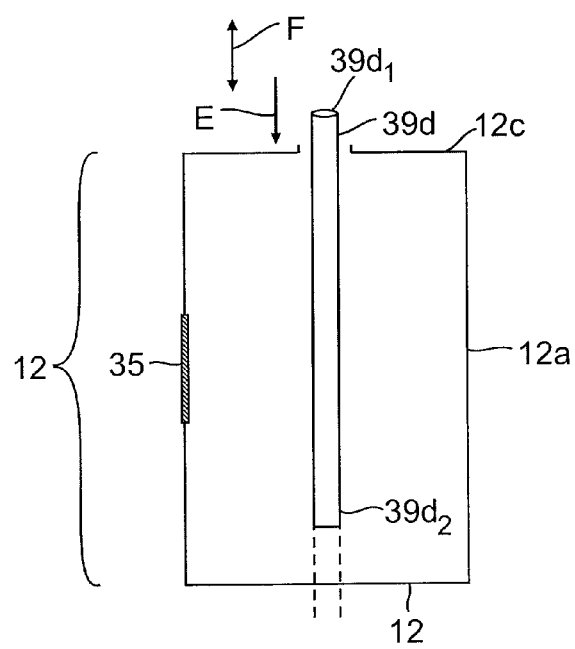
FIG. 17D is an interior side view schematic diagram of a catheter or a guide wire, the catheter or the guide wire being a treatable target itself or alternatively being a target support structure, in accordance with a further embodiment of the present invention.

Referring next to FIG. 17D, this interior side view schematic diagram illustrates a treatable target 14 (as described, supra) in the form of a catheter or a guide wire 39d disposed through at least one sidewall 12c of the chamber 12, by example only, in accordance with a further embodiment of the present invention. The catheter or the guide wire 39d is inserted through at least one sidewall 12c of chamber 12, and optionally exit through an opposing sidewall 12c. The catheter or the guide wire 39d may be alternatively inserted and removed in a direction F through one opening in the sidewall 12c. An optional door (not shown) may be provided to reduce the opening in the sidewall once the catheter or the guide wire 39d is inserted, thereby increasing the irradiance and radiative uniformity within the chamber 12. This embodiment facilitates treating surface coatings on catheters and guide wires 39d.

Still referring next to FIG. 17D, the catheter or the guide wire 39d may alternatively act as a target support structure, wherein the catheter or the guide wire 39d is disposed through at least one sidewalls 12c of the chamber 12, as previously described, but can also be used for supporting, feeding, and/or flowing a treatable target 14 (as described, supra), by example only, in accordance with a further embodiment of the present invention. The treatable target 14 (as described, supra) may be inserted through a first end $39d_1$ of the catheter or the guide wire 39d, and may be optionally fed, flowed, or otherwise conveyed through the catheter or the guide wire 39d to a second end $39d_2$ of the catheter or the guide wire 39d in a direction E, by example only. The catheter or the guide wire 39d may be alternatively inserted and removed in direction F through only one opening in the sidewall 12c. This embodiment is conducive to use with a treatable target 14 (as described, supra) that comprises a solid, a gel, or a fluid, such as water, oil, or gas.

Figure 17E:
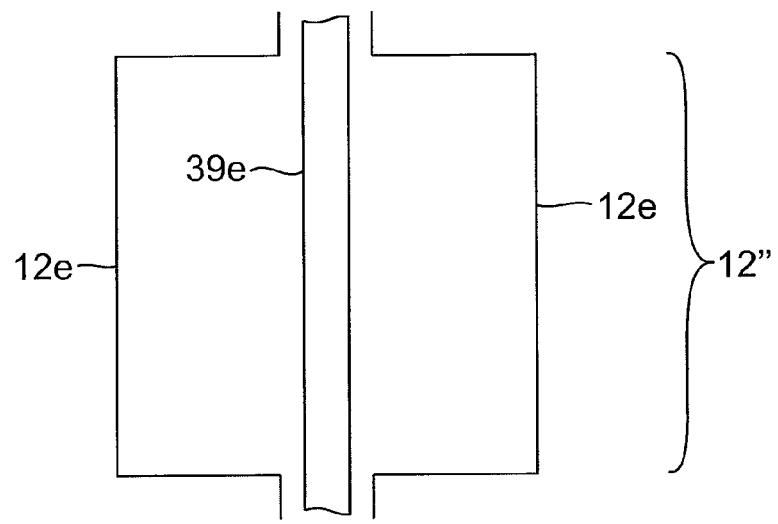
FIG. 17E is an interior side view schematic diagram of an elongated element disposed in a split chamber, the elongated element being a treatable target itself or alternatively being a target support structure, in accordance with a further embodiment of the present invention.

Referring next to FIG. 17E, this interior side view schematic diagram illustrates a treatable target 14 (as described, supra) in the form of an elongated element 39e, such as a continuous pipe 39c (FIG. 17C) or a catheter or guide wire 39d (FIG. 17D), by example only, disposed in a split chamber 12″, by example only, in accordance with a further embodiment of the present invention. The split chamber 12″ comprises two partial chamber portions 12e, wherein one partial chamber portion 12e or both partial chamber portions 12e are transversably movable in relation to the axis of the elongated element 39e. The elongated element 39e is surrounded by both partial chamber portions 12e, wherein a loss of light is minimized between both partial chamber portions 12e and the elongated element 39e is largely uniformly illuminated. Once the treatment is completed, the partial chamber portions 12e are moved apart such that sufficient space is provided for removing the elongated element 39e and any supporting structure (not shown) from the chamber 12″. By closing the partial chamber portions 12e around the elongated element 39e, the irradiance and radiative uniformity is improved. Further, by separating the chamber 12″ into two partial chamber portions 12e and providing an opening between the partial chamber portions 12e, large target support structures may be used without degrading the performance of the chamber 12″ by closing the chamber portions only around the elongated element 39e and excluding the target support structure from the chamber interior volume. This embodiment also facilitates treating surface coatings on elongated elements 39e. Alternatively, the elongated element 39e may, itself, act as a conduit for supporting and conveying a treatable object 14 (as described, supra).

Figure 18:
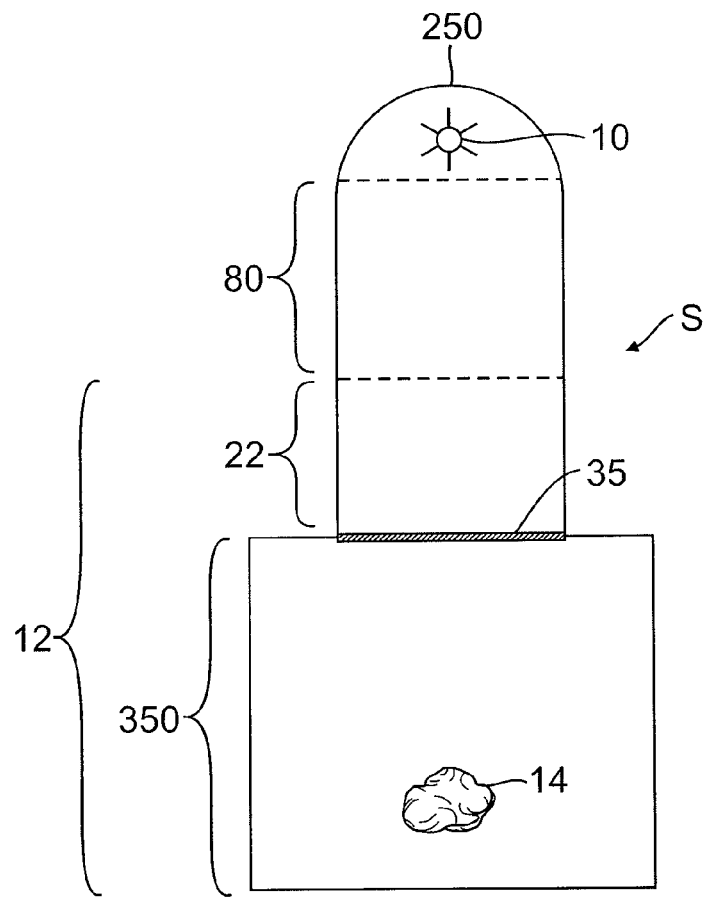
FIG. 18 is an interior view schematic diagram of an integrating optical system, further comprising a coupling device, the coupling device being optically coupled with both the lamp assembly and the chamber, in accordance with yet a further embodiment of the present invention.

Referring next to FIG. 18, this schematic diagram illustrates an integrating optical system S, as shown in FIG. 5A, further comprising a coupling device 80, the coupling device 80 being optically coupled with both the lamp assembly 200 and the chamber 12, in accordance with yet a further embodiment of the present invention. The chamber 12 may comprise a main chamber 350 and in some cases, an auxiliary chamber 22. The lamp assembly 200 may not be directly coupled to the chamber 12. Rather, in this embodiment, the lamp assembly 200 is coupled to the chamber 12 by way of the coupling device 80, the coupling device 80 comprising an element, such as one or more of a light guide, a reflector, a lens, or other optical element, to transmit light from the lamp assembly 200 to the chamber 12. That is, in some embodiments, the coupling device 80 optically couples the light from the lamp assembly 200 to the chamber 12. In some embodiments, the light guide (not shown) comprises an element, such as one or more of an optical liquid, an optical fiber, or other optical transmitting medium. In some embodiments, the use of a lens (not shown) facilitates collection of light from the light source 10 and facilitates transmission of the light to the chamber 12. Further, the coupling device 80 may comprise the light guide used in combination with at least one lens. In some embodiments, the at least one lens is disposed at either end of the light guide for facilitating collection of light from the light source 10, for facilitating transmission to the chamber 12, and for facilitating the distribution of light into the chamber 12. By example only, a desired distribution of light may be focused or collimated for a given application. Furthermore, the coupling device 80 may be used in conjunction with any of the foregoing embodiments, such as those described in relation to FIGS. 3A-17E.

In some embodiments of the present invention, the chamber 12 comprises any suitable configuration, such as a sphere, a rectanguloid, a cube, a polyhedron, an ellipsoid, an ogivoid, a paraboloid, a cylinder, a hyperboloid of one sheet, a hyperboloid of two sheets, a hyperbolic paraboloid, and an elliptical cone, for accommodating a work-piece. In relation to the chamber 12, the treatable target 14 comprises a surface having a plurality of points; wherein any point of the plurality of points being irradiated by light incident through the at least one diffuse transmissive baffle 35 also is irradiated by light incident from at least one other point in the system S other than through the at least one diffuse transmissive baffle 35. The at least one treatable target 14 comprises a material that is responsive to ultraviolet light, such as an ultraviolet-curable polymeric material, a radiation-curable material, a free-radical-polymerizable material, a disinfectable material, a weatherable material, and an artificially weatherable material.

Information as herein shown and described in detail is fully capable of attaining one or more objects of embodiments of the invention, the presently preferred embodiment of the invention, and is, thus, representative of the subject matter which is broadly contemplated by embodiments of the present invention. The scope of the present invention fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments that are known to those of ordinary skill in the art are hereby expressly incorporated by reference and are intended to be encompassed by the present claims.

Moreover, no requirement exists for a system or method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, that various changes and modifications in form, material, and fabrication material detail may be made, without departing from the spirit and scope of the invention as set forth in the appended claims, should be readily apparent to those of ordinary skill in the art.

What is claimed:

1. An integrating optical system, comprising:
at least one chamber, each at least one chamber having at least one aperture and at least one portion comprising a diffuse reflective material;
at least one light source disposed outside of the at least one chamber and oriented to provide light rays into the at least one chamber through the aperture; and
at least one diffuse transmissive baffle disposed in relation to the at least one chamber and the aperture such that all light rays from the at least one light source entering the at least one chamber pass through the aperture and the at least one diffuse transmissive baffle and the at least one diffuse transmissive baffle is also disposed in an optical path between the at least one light source and at least one treatable target, wherein at least one light-ray originating from the at least one light source is diffusely transmitted from the at least one diffuse transmissive baffle and impinges on an interior surface of the at least one chamber before impinging on the at least one treatable target, wherein the interior surface comprises the diffuse reflective material, and wherein at least one light-ray originating from the at least one light source is diffusely transmitted from the at least one diffuse transmissive baffle and impinges directly on the at least one treatable target without first impinging of the interior surface of the at least one chamber;
wherein a distance between the at least one diffuse transmissive baffle and the at least one treatable target is such that less than 15% of light rays transmitting through the at least one diffuse transmissive baffle impinge directly on the at least one treatable target, and such that more than 85% of the light rays transmitting through the at least one diffuse transmissive baffle impinge directly on the interior surface before impinging on the at least one treatable target;
wherein the diffuse reflective material scatters the at least one light ray substantially uniformly into all directions in a hemisphere adjacent to an incident side of the diffuse reflective material;
wherein the at least one light source comprises at least one element selected from a group consisting essentially of a microwave-excited arc lamp, a medium pressure arc lamp, a high pressure arc lamp, a light emitting diode, and a laser;
wherein the at least one light source is configured to output light rays having a non-visible component suitable to treat the at least one treatable target; and
wherein the at least one treatable target comprises a material which at least one property thereof is altered by the light rays from the at least one light source.

2. The system of claim 1, wherein the at least one diffuse transmissive baffle facilitates passage of light from the at least one light source therethrough in a diffuse manner.

3. The system of claim 1, wherein the at least one chamber comprises at least one configuration selected from a group consisting essentially of a sphere, a rectanguloid, a cube, a polyhedron, an ellipsoid, an ogivoid, a paraboloid, a cylinder, a hyperboloid of one sheet, a hyperboloid of two sheets, a hyperbolic paraboloid, and an elliptical cone.

4. The system of claim 1,
wherein the at least one diffuse transmissive baffle comprises a plurality of diffuse transmissive baffles in a stacking relationship, and
wherein the plurality of diffuse transmissive baffles comprises at least one configuration selected from a group consisting essentially of a spacing being disposed between each baffle of the plurality of diffuse transmissive baffles and each baffle being adjacently disposed and contacting another baffle of the plurality of diffuse transmissive baffles.

5. The system of claim 1, wherein the at least one diffuse transmissive baffle comprises at least one material selected from a group consisting essentially of a high-temperature-resistant material, an aluminum oxide, a polycrystalline aluminum oxide, a polycrystalline sapphire, an optical filter, a quartz, an opaled quartz, a fitted quartz, a sandblasted quartz, a bead-blasted quartz, a sapphire, a sandblasted sapphire, a bead-blasted sapphire, an acid-etched quartz, an acid-etched sapphire, a ground quartz, and a ground sapphire.

6. The system of claim 1, wherein the at least one diffuse transmissive baffle comprises at least one material selected from a group consisting essentially of a volume diffusing material, a pot opal, a quartz having a distribution of voids, a quartz having a distribution of scattering sites, a quartz having a distribution of impurities, a quartz having a distribution of dopants, a quartz felt, a quartz wool, and a randomly oriented transmissive fiber sandwiched between optically transparent support members.

7. The system of claim 1, wherein the at least one diffuse transmissive baffle comprises at least one diffusing surface formed by at least one technique consisting essentially of etching, chemical etching, acid etching, sandblasting, bead-blasting, grinding, and opaling.

8. The system of claim 1, wherein the at least one diffuse transmissive baffle comprises a polished surface and a diffusing surface.

9. The system of claim 8, wherein the polished surface comprises a dichroic material for reflecting at least one type of light selected from a group consisting essentially of infrared light, visible light, and ultraviolet light.

10. The system of claim 1, wherein the at least one chamber comprises a main chamber and an auxiliary chamber, the auxiliary chamber disposed between the at least one light source and the main chamber.

11. The system of claim 1, wherein the diffuse reflective material comprises at least one material selected from a group consisting essentially of a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate.

12. The system of claim 1, further comprising at least one shutter disposed between the at least one light source and the at least one chamber.

13. The system of claim 1, further comprising at least one lamp assembly, each at least one lamp assembly comprising at least one light reflector for accommodating the at least one light source,
wherein the at least one light reflector facilitates reflection of light toward the at least one chamber,
wherein the at least one light reflector comprises a feature selected from a group consisting essentially of a diffuse reflective surface and a specular reflective surface, and
wherein the at least one lamp assembly comprises a focus characteristic selected from a group consisting essentially of in-focus and out-of-focus.

14. The system of claim 13, further comprising at least one coupling device, the at least one coupling device being optically coupled with both the at least one lamp assembly and the at least one chamber.

15. The system of claim 14, wherein the at least one coupling device comprises at least one element selected from a group consisting essentially of a light guide and a lens for facilitating transmission of light from the at least one lamp assembly to the at least one chamber.

16. The system of claim 1,
wherein the material comprises at least one material selected from a group consisting essentially of an ultraviolet-curable polymeric material, a radiation-curable material, a free-radical-polymerizable material, a disinfectable material, a weatherable material, and an artificially weatherable material.

17. The system of claim 1, further comprising at least one hot mirror disposed between the at least one light source and the at least one treatable target.

18. The system of claim 1,
wherein the at least one diffuse transmissive baffle facilitates passage of light from the at least one light source therethrough in a diffuse manner,
wherein the at least one diffuse transmissive baffle comprises at least one material selected from a group consisting essentially of a high-temperature-resistant material, an aluminum oxide, a polycrystalline aluminum oxide, a polycrystalline sapphire, an optical filter, a quartz, an opaled quartz, a fritted quartz, a sandblasted quartz, a bead-blasted quartz, a sapphire, a sandblasted sapphire, a bead-blasted sapphire, an acid-etched quartz, an acid-etched sapphire, a ground quartz, and a ground sapphire,
wherein the at least one diffuse transmissive baffle comprises at least one material selected from a group consisting essentially of a volume diffusing material, a pot opal, a quartz having a distribution of voids, a quartz having a distribution of scattering sites, a quartz having a distribution of impurities, a quartz having a distribution of dopants, a quartz felt, a quartz wool, and a randomly oriented transmissive fiber sandwiched between optically transparent support members,
wherein the at least one diffuse transmissive baffle comprises at least one diffusing surface,
wherein the at least one diffusing surface is formed by at least one technique consisting essentially of etching, chemical etching, acid etching, sandblasting, bead-blasting, grinding, and opaling, and
wherein the diffuse reflective material comprises at least one material selected from a group consisting essentially of a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate.

19. The system of claim 18, further comprising at least one shutter disposed between the at least one light source and the at least one chamber.

20. The system of claim 18, wherein the at least one diffuse transmissive baffle further comprises a polished surface.

21. The system of claim 20, wherein the polished surface comprises a dichroic material for reflecting at least one type of light selected from a group consisting essentially of infrared light and visible light.

22. The integrating optical system of claim 1, wherein the at least one diffuse transmissive baffle is spaced apart from the at least one light source.

23. The integrating optical system of claim 1 wherein the at least one diffuse transmissive baffle is a separate component from and not integrated into the at least one light source.

24. The integrating optical system of claim 1, wherein the at least one diffuse transmissive baffle comprises a polished surface facing the at least one light source and a diffusing surface facing away from the at least one light source.

25. The system of claim 1, wherein the at least one diffuse transmissive baffle comprises a plurality of diffuse transmissive baffles in a stacking relationship, and a spacing being disposed between each baffle of the plurality of diffuse transmissive baffles.

26. The system of claim 1, wherein, due to the at least one diffuse transmissive baffle and the at least one portion of the chamber comprising the diffuse reflective material, the system does not comprise a diffuse reflective baffle.

27. The system of claim 1, wherein the more than 85% of the light rays transmitting through the at least one diffuse transmissive baffle impinge directly on the interior surface without impinging on any other intermediary surface before impinging on the at least one treatable target.

28. The system of claim 1, wherein the diffuse reflective material scatters the at least one light-ray in directions including an incoming direction of the at least one light-ray.

29. The system of claim 1, wherein diffuse reflective material is an isotropic material.

30. The system of claim 1, wherein the diffuse transmissive baffle transmits and scatters the at least one light-ray substantially uniformly into all directions in a hemisphere adjacent to a through side of the diffuse transmissive baffle.

31. The system of claim 1, wherein the at least one chamber does not include a non-transmissive baffle positioned between the transmissive baffle and the treatable target.

32. The system of claim 1, wherein the diffuse reflective material produces substantially Lambertian reflectance.

33. A method of fabricating an integrating optical system, comprising:
providing at least one chamber having at least one aperture and at least one portion comprising a diffuse reflective material;
providing at least one light source disposed outside of the at least one chamber and oriented to provide light rays into the at least one chamber through the aperture; and
providing at least one diffuse transmissive baffle disposed in relation to the at least one chamber and the aperture such that all light rays from the at least one light source entering the at least one chamber pass through the aperture and the at least one diffuse transmissive baffle and the at least one diffuse transmissive baffle is also disposed in an optical path between the at least one light source and at least one treatable target, wherein the at least one diffuse transmissive baffle is disposed in a manner wherein at least one light-ray originating from the at least one light source is diffusely transmittable from the at least one diffuse transmissive baffle and impingeable on an interior surface of the at least one chamber before being impingeable on the at least one treatable target, wherein the interior surface comprises the diffuse reflective material, and wherein at least one light-ray originating from the at least one light source is diffusely transmitted from the at least one diffuse transmissive baffle and impinges directly on the at least one treatable target without first impinging of the interior surface of the at least one chamber;
wherein a distance between the at least one diffuse transmissive baffle and the at least one treatable target is such that less than 15% of light rays transmitting through the at least one diffuse transmissive baffle impinge directly on the at least one treatable target, and such that more than 85% of the light rays transmitting through the at least one diffuse transmissive baffle impinge directly on the interior surface before impinging on the at least one treatable target;
wherein the diffuse reflective material is configured to scatter the at least one light ray substantially uniformly into all directions in a hemisphere on an incident side of the diffuse reflective material;
wherein the at least one light source comprises at least one element selected from a group consisting essentially of a microwave-excited arc lamp, a medium pressure arc lamp, a high pressure arc lamp, a light emitting diode, and a laser;
wherein the at least one light source is configured to output light rays having a non-visible component suitable to treat the at least one treatable target; and
wherein the at least one treatable target comprises a material which at least one property thereof is altered by the light rays from the at least one light source.

34. The method of claim 33, further comprising providing at least one shutter disposed between the at least one light source and the at least one chamber.

35. The method of claim 33, further comprising providing at least one lamp assembly, the at least one lamp assembly providing step comprising providing each at least one lamp assembly with at least one light reflector for accommodating the at least one light source, the at least one light reflector facilitating reflection of light toward the at least one chamber.

36. A method of treating at least one treatable target with light, comprising:
providing light, having light rays, within a volume from at least one light source disposed outside of at least one chamber and oriented to provide the light rays into the at least one chamber through an aperture, wherein all of the light rays entering the at least one chamber pass through the aperture and at least one diffuse transmissive baffle;
diffusely transmitting, using the at least one diffuse transmissive baffle, the all of the light rays entering the at least one chamber such that at least one first light-ray originating from the at least one light source and being in a direct path to the at least one treatable target is diffusely transmitted from the at least one diffuse transmissive baffle and impinges on an interior surface of at least one chamber before impinging on the at least one treatable target, and such that at least one second light-ray originating from the at least one light source is diffusely transmitted from the at least one diffuse transmissive baffle and impinges directly on the at least one treatable target without first impinging of the interior surface of the at least one chamber;
wherein a distance between the at least one diffuse transmissive baffle and the at least one treatable target is such that less than 15% of light rays transmitting through the at least one diffuse transmissive baffle impinge directly on the at least one treatable target, and such that more than 85% of the light rays transmitting through the at least one diffuse transmissive baffle impinge directly on the interior surface before impinging on the at least one treatable target;
diffusely reflecting, at the interior surface, the at least one first light-ray within the volume from a diffuse reflective material by scattering the at least one first light-ray substantially uniformly in all directions in a hemisphere adjacent to an incident surface of the diffuse reflective material for collecting the at least one first light-ray, thereby integrating the at least one first light-ray, and thereby providing at least one integrated first light-ray; and
irradiating the at least one treatable target with the at least one integrated first light-ray and the at least one second light ray, thereby providing at least one treated target;
wherein the at least one light source comprises at least one element selected from a group consisting essentially of a microwave-excited arc lamp, a medium pressure arc lamp, a high pressure arc lamp, a light emitting diode, and a laser;
wherein the at least one light source is configured to output light rays having a non-visible component suitable to treat the at least one treatable target; and
wherein the at least one treatable target comprises a material which at least one property thereof is altered by the light rays from the at least one light source.

* * * * *